US006821787B2

United States Patent
Neilson et al.

(10) Patent No.: US 6,821,787 B2
(45) Date of Patent: Nov. 23, 2004

(54) APPARATUS AND METHODS FOR INFRARED CALORIMETRIC MEASUREMENTS

(75) Inventors: Andy C. Neilson, Groton, MA (US); Michael R. Sweeney, Stoneham, MA (US); James D. Orrell, III, Bothell, WA (US); Marc Sampson, Laval (CA); John M. Hopkins, Shoreline, WA (US); Michael W. Oster, Seattle, WA (US)

(73) Assignee: Thermogenic Imaging, Inc., North Billerica, MA (US)

( * ) Notice: Subject to any disclaimer, the term of this patent is extended or adjusted under 35 U.S.C. 154(b) by 514 days.

(21) Appl. No.: 10/001,892

(22) Filed: Nov. 19, 2001

(65) Prior Publication Data

US 2002/0146345 A1 Oct. 10, 2002

Related U.S. Application Data

(63) Continuation-in-part of application No. 09/777,363, filed on Feb. 5, 2001, and a continuation-in-part of application No. 09/777,368, filed on Feb. 5, 2001, and a continuation-in-part of application No. 09/777,364, filed on Feb. 5, 2001, and a continuation of application No. 09/764,963, filed on Jan. 17, 2001.
(60) Provisional application No. 60/249,931, filed on Nov. 17, 2000, and provisional application No. 60/256,852, filed on Dec. 19, 2000.

(51) Int. Cl.⁷ ............................................. G01N 21/01
(52) U.S. Cl. .................... 436/149; 436/150; 436/164; 422/82.05; 422/82.12

(58) Field of Search .................. 422/55, 68.1, 82.01, 422/82.05, 82.08, 82.09, 83, 99, 102, 82.12; 436/149, 150, 164, 165, 166, 174; 356/335, 336, 337

(56) References Cited

U.S. PATENT DOCUMENTS 2,056,791 A  10/1936  Logan
3,013,467 A  12/1961  Minsky (List continued on next page.)

FOREIGN PATENT DOCUMENTS

DE  29805613 U1  7/1998
EP  0 204 109 A2  12/1986

(List continued on next page.)

OTHER PUBLICATIONS

*Infrared Thermogenic Screening of Combinatorial Libraries of Heterogeneous Catalysts*, Moates et al., *Ind. Eng. Chem. Res.*, vol. 35, No. 12, pp. 4801–4803, 1996.

(List continued on next page.)

Primary Examiner—Jeffrey R. Snay
(74) Attorney, Agent, or Firm—Kolisch Hartwell, P.C.

(57) ABSTRACT

Apparatus and methods for performing calorimetry. The apparatus include optical devices for detecting thermal processes and multiwell sample plates for supporting samples for use with such optical devices. The methods include measurement strategies and data processing techniques for reducing noise in measurements of thermal processes. The apparatus and methods may be particularly suitable for extracting thermal data from small differential measurements made using an infrared camera and for monitoring chemical and physiological processes.

43 Claims, 9 Drawing Sheets

U.S. PATENT DOCUMENTS

| | | |
|---|---|---|
| 3,540,858 A | 11/1970 | Rochte et al. |
| 3,849,654 A | 11/1974 | Malvin |
| 4,011,451 A | 3/1977 | Nelson |
| 4,024,560 A | 5/1977 | Miller et al. |
| 4,053,381 A | 10/1977 | Hamblen et al. |
| 4,067,653 A | 1/1978 | Fletcher et al. |
| 4,162,896 A | 7/1979 | Hosli |
| 4,221,966 A | 9/1980 | Kerr et al. |
| 4,231,989 A | 11/1980 | Thoma |
| 4,240,751 A | 12/1980 | Linnecke et al. |
| 4,245,052 A | 1/1981 | Lund |
| 4,292,273 A | 9/1981 | Butz et al. |
| 4,332,768 A | 6/1982 | Berglund |
| 4,397,560 A | 8/1983 | Andresen |
| 4,461,328 A | 7/1984 | Kenney |
| 4,498,510 A | 2/1985 | Minshew, Jr. et al. |
| 4,501,970 A | 2/1985 | Nelson |
| 4,545,958 A | 10/1985 | Dopatka |
| 4,591,550 A | 5/1986 | Hafeman et al. |
| 4,599,315 A | 7/1986 | Terasaki et al. |
| 4,622,208 A | 11/1986 | Namba et al. |
| 4,626,684 A | 12/1986 | Landa |
| 4,669,978 A | 6/1987 | Klefisch |
| 4,670,219 A | 6/1987 | Nelson et al. |
| 4,704,255 A | 11/1987 | Jolley |
| 4,704,353 A | 11/1987 | Humphries et al. |
| 4,707,067 A | 11/1987 | Haberland et al. |
| 4,730,921 A | 3/1988 | Klein et al. |
| 4,735,778 A | 4/1988 | Maruyama et al. |
| 4,738,825 A | 4/1988 | Kelln et al. |
| 4,741,619 A | 5/1988 | Humphries et al. |
| 4,762,420 A | 8/1988 | Bowley |
| 4,772,453 A | 9/1988 | Lisenbee |
| 4,788,150 A | 11/1988 | Nelson et al. |
| 4,801,804 A | 1/1989 | Rosenthal |
| 4,810,096 A | 3/1989 | Russell et al. |
| D303,149 S | 8/1989 | Andersen |
| 4,868,103 A | 9/1989 | Stavrianopoulos et al. |
| 4,873,633 A | 10/1989 | Mezei et al. |
| 4,874,948 A | 10/1989 | Cielo et al. |
| 4,883,579 A | 11/1989 | Humphries et al. |
| 4,892,409 A | 1/1990 | Smith |
| 4,894,347 A | 1/1990 | Hillyard et al. |
| 4,931,402 A | 6/1990 | Abplanalp |
| 4,936,682 A | 6/1990 | Hoyt |
| 4,948,442 A | 8/1990 | Manns |
| 4,968,148 A | 11/1990 | Chow et al. |
| 4,979,093 A | 12/1990 | Laine et al. |
| 4,979,821 A | 12/1990 | Schutt et al. |
| 5,002,889 A | 3/1991 | Klein |
| 5,017,019 A | 5/1991 | Pompei |
| 5,047,215 A | 9/1991 | Manns |
| 5,056,525 A | 10/1991 | Hafezi |
| 5,084,246 A | 1/1992 | Lyman et al. |
| 5,086,022 A | 2/1992 | Roca et al. |
| 5,091,652 A | 2/1992 | Mathies et al. |
| 5,110,556 A | 5/1992 | Lyman et al. |
| 5,112,134 A | 5/1992 | Chow et al. |
| 5,169,601 A | 12/1992 | Ohta et al. |
| 5,178,019 A | 1/1993 | Keiter |
| 5,198,670 A | 3/1993 | VanCauter et al. |
| 5,199,436 A | 4/1993 | Pompei et al. |
| 5,204,268 A | 4/1993 | Matsumoto |
| 5,206,568 A | 4/1993 | Björnson et al. |
| 5,207,987 A | 5/1993 | Kureshy et al. |
| 5,208,161 A | 5/1993 | Saunders et al. |
| 5,216,488 A | 6/1993 | Tuunanen et al. |
| 5,225,164 A | 7/1993 | Astle |
| 5,262,128 A | 11/1993 | Leighton et al. |
| 5,273,718 A | 12/1993 | Sköld et al. |
| 5,275,951 A | 1/1994 | Chow et al. |
| 5,287,758 A | 2/1994 | Geiss et al. |
| 5,296,195 A | 3/1994 | Pang et al. |
| 5,307,144 A | 4/1994 | Hiroshi et al. |
| 5,319,436 A | 6/1994 | Manns et al. |
| 5,340,747 A | 8/1994 | Eden |
| 5,341,215 A | 8/1994 | Seher |
| 5,349,436 A | 9/1994 | Fisch |
| 5,355,215 A | 10/1994 | Schroeder et al. |
| 5,376,335 A | 12/1994 | Gleaves |
| 5,381,796 A | 1/1995 | Pompei |
| 5,384,093 A | 1/1995 | Ootani et al. |
| 5,386,831 A | 2/1995 | Gluck |
| 5,401,465 A | 3/1995 | Smethers et al. |
| 5,436,718 A | 7/1995 | Fernandes et al. |
| 5,443,791 A | 8/1995 | Cathcart et al. |
| 5,445,157 A | 8/1995 | Adachi et al. |
| 5,445,158 A | 8/1995 | Pompei |
| 5,449,921 A | 9/1995 | Baba |
| 5,457,527 A | 10/1995 | Manns et al. |
| 5,459,300 A | 10/1995 | Kasman |
| 5,469,855 A | 11/1995 | Pompei et al. |
| 5,487,872 A | 1/1996 | Hafeman et al. |
| 5,497,670 A | 3/1996 | Carl |
| 5,508,197 A | 4/1996 | Hansen et al. |
| 5,512,492 A | 4/1996 | Herron et al. |
| 5,516,490 A | 5/1996 | Sanadi |
| 5,527,684 A | 6/1996 | Mabile et al. |
| 5,531,697 A | 7/1996 | Olsen et al. |
| 5,531,698 A | 7/1996 | Olsen |
| 5,540,889 A | 7/1996 | Gordon et al. |
| 5,542,012 A | 7/1996 | Fernandes et al. |
| 5,560,811 A | 10/1996 | Briggs et al. |
| 5,589,136 A | 12/1996 | Northrup et al. |
| 5,589,350 A | 12/1996 | Bochner |
| 5,589,351 A | 12/1996 | Harootunian |
| 5,592,289 A | 1/1997 | Norris |
| 5,599,500 A | 2/1997 | Jones |
| 5,604,130 A | 2/1997 | Warner et al. |
| 5,615,672 A | 4/1997 | Braig et al. |
| 5,620,894 A | 4/1997 | Barger et al. |
| 5,628,323 A | 5/1997 | Pompei |
| 5,633,724 A | 5/1997 | King et al. |
| 5,645,800 A | 7/1997 | Masterson et al. |
| 5,650,125 A | 7/1997 | Bosanquet |
| 5,653,239 A | 8/1997 | Pompei et al. |
| 5,655,839 A | 8/1997 | Schmidt et al. |
| 5,663,545 A | 9/1997 | Marquiss |
| 5,664,578 A | 9/1997 | Boczän |
| 5,666,962 A | 9/1997 | Lamey |
| 5,670,113 A | 9/1997 | Akong et al. |
| 5,677,196 A | 10/1997 | Herron et al. |
| 5,678,566 A | 10/1997 | Dribbon |
| 5,679,310 A | 10/1997 | Manns |
| 5,693,942 A | 12/1997 | Endo et al. |
| 5,736,410 A | 4/1998 | Zarling et al. |
| 5,738,825 A | 4/1998 | Rudigier et al. |
| 5,738,827 A | 4/1998 | Marquiss |
| 5,740,809 A | 4/1998 | Baratta |
| 5,750,410 A | 5/1998 | Dou et al. |
| 5,756,050 A | 5/1998 | Ershow et al. |
| 5,756,304 A | 5/1998 | Jovanovich |
| 5,759,494 A | 6/1998 | Szlosek |
| 5,766,875 A | 6/1998 | Hafeman et al. |
| 5,770,151 A | 6/1998 | Roach et al. |
| 5,771,261 A | 6/1998 | Anbar |
| 5,772,966 A | 6/1998 | Maracas et al. |
| 5,772,967 A | 6/1998 | Wannlund et al. |
| 5,774,214 A | 6/1998 | Prettyjohns |
| 5,780,857 A | 7/1998 | Harju et al. |
| 5,790,586 A | 8/1998 | Hilton, Jr. et al. |

| | | |
|---|---|---|
| 5,795,305 A | 8/1998 | Cho et al. |
| 5,798,035 A | 8/1998 | Kirk et al. |
| 5,798,085 A | 8/1998 | Seaton et al. |
| 5,800,778 A | 9/1998 | Chen et al. |
| 5,801,055 A | 9/1998 | Henderson |
| 5,810,010 A | 9/1998 | Anbar |
| 5,811,256 A | 9/1998 | Bryant |
| 5,813,982 A | 9/1998 | Baratta |
| 5,820,263 A | 10/1998 | Ciobanu |
| 5,820,264 A | 10/1998 | Tsao et al. |
| 5,840,256 A | 11/1998 | Demers et al. |
| 5,842,582 A | 12/1998 | DeStefano, Jr. |
| 5,846,708 A | 12/1998 | Hollis et al. |
| 5,853,894 A | 12/1998 | Brown |
| 5,858,309 A | 1/1999 | Mathus et al. |
| 5,873,394 A | 2/1999 | Meltzer |
| 5,873,833 A | 2/1999 | Pompei |
| 5,874,048 A | 2/1999 | Seto et al. |
| 5,879,632 A | 3/1999 | Demers |
| 5,882,597 A | 3/1999 | Astle |
| 5,882,930 A | 3/1999 | Baier |
| 5,888,454 A | 3/1999 | Leistner et al. |
| 5,891,619 A | 4/1999 | Zakim et al. |
| 5,893,833 A | 4/1999 | Pompei et al. |
| 5,910,287 A | 6/1999 | Cassin et al. |
| 5,911,953 A | 6/1999 | Ogata et al. |
| 5,924,996 A | 7/1999 | Cho et al. |
| 5,933,232 A | 8/1999 | Atzler et al. |
| 5,941,833 A | 8/1999 | Lipman |
| 5,958,694 A | 9/1999 | Nikiforov |
| 5,959,297 A | 9/1999 | Weinberg et al. |
| 5,961,466 A | 10/1999 | Anbar |
| 5,961,926 A | 10/1999 | Kolb et al. |
| 5,989,835 A | 11/1999 | Dunlay et al. |
| 5,993,746 A | 11/1999 | Priha et al. |
| 5,995,865 A | 11/1999 | Carioni |
| 5,999,842 A | 12/1999 | Harrison et al. |
| 5,999,843 A | 12/1999 | Anbar |
| 6,018,388 A | 1/2000 | Nawracala et al. |
| 6,021,253 A | 2/2000 | Bell |
| 6,022,141 A | 2/2000 | Bass |
| 6,023,637 A | 2/2000 | Liu et al. |
| 6,025,985 A | 2/2000 | Leytes et al. |
| 6,027,695 A | 2/2000 | Oldenburg et al. |
| 6,030,342 A | 2/2000 | Amano et al. |
| 6,030,917 A | 2/2000 | Weinberg et al. |
| 6,033,605 A | 3/2000 | Szlosek |
| 6,045,257 A | 4/2000 | Pompei et al. |
| 6,045,755 A | 4/2000 | Lebl et al. |
| 6,047,205 A | 4/2000 | Pompei |
| 6,054,325 A | 4/2000 | Kedar et al. |
| 6,056,435 A | 5/2000 | Pompei |
| 6,063,633 A | 5/2000 | Willson, III |
| 6,071,748 A | 6/2000 | Modlin et al. |
| 6,083,761 A | 7/2000 | Kedar et al. |
| 6,090,050 A | 7/2000 | Constantinides |
| 6,097,025 A | 8/2000 | Modlin et al. |
| 6,114,178 A | 9/2000 | Dezael et al. |
| 6,129,673 A | 10/2000 | Fraden |
| 6,157,854 A | 12/2000 | Haber et al. |
| 6,159,425 A | 12/2000 | Edwards et al. |
| 6,172,367 B1 | 1/2001 | Fritz et al. |
| 6,187,267 B1 | 2/2001 | Taylor et al. |
| 6,190,329 B1 | 2/2001 | Cheng |
| 6,195,445 B1 | 2/2001 | Dubuisson-Jolly et al. |
| 6,203,193 B1 | 3/2001 | Egawa |
| 6,207,369 B1 | 3/2001 | Wohlstadter et al. |
| 6,208,749 B1 | 3/2001 | Gutkowicz-Krusin et al. |
| 6,212,824 B1 | 4/2001 | Orr et al. |
| 6,242,262 B1 | 6/2001 | Morken et al. |
| 6,248,066 B1 | 6/2001 | Barnett et al. |
| 6,272,375 B1 | 8/2001 | Katzir et al. |
| 6,292,685 B1 | 9/2001 | Pompei |
| 6,299,347 B1 | 10/2001 | Pompei |
| 6,306,658 B1 | 10/2001 | Turner et al. |
| 6,333,196 B1 | 12/2001 | Willson, III |
| 6,373,570 B1 | 4/2002 | McFarland et al. |
| 6,380,605 B1 | 4/2002 | Verhaegen |
| 2001/0046471 A1 | 11/2001 | Marek et al. |

FOREIGN PATENT DOCUMENTS

| | | |
|---|---|---|
| EP | 0 266 881 A2 | 5/1988 |
| EP | 0 259 386 B1 | 4/1991 |
| EP | 0 542 422 A1 | 5/1993 |
| EP | 0 977 037 A1 | 2/2000 |
| EP | 1 003 020 A1 | 5/2000 |
| EP | 1 003 039 A1 | 5/2000 |
| WO | WO94/29024 | 12/1994 |
| WO | WO99/04228 | 1/1998 |
| WO | WO98/15813 | 4/1998 |
| WO | WO98/46981 | 10/1998 |
| WO | WO99/08233 | 2/1999 |
| WO | WO99/23466 | 5/1999 |
| WO | WO99/37203 | 7/1999 |
| WO | WO99/42817 | 8/1999 |
| WO | WO99/54711 | 10/1999 |
| WO | WO99/60630 | 11/1999 |
| WO | WO00/04364 | 1/2000 |
| WO | WO00/05336 | 2/2000 |
| WO | WO00/06989 | 2/2000 |
| WO | WO00/06990 | 2/2000 |
| WO | WO00/06991 | 2/2000 |
| WO | WO00/42209 | 7/2000 |
| WO | WO00/50877 | 8/2000 |
| WO | WO00/55372 | 9/2000 |
| WO | WO00/66269 | 11/2000 |
| WO | WO01/04608 | 1/2001 |
| WO | WO01/85901 | 11/2001 |
| WO | WO02/11881 | 2/2002 |

OTHER PUBLICATIONS

PCR Reaction Vessels brochure, Corning Costar Corporation, Sep. 1996.

Miniprep 50 Mini Sample Processor brochure, Tecan AG, Jun. 1997.

Advanced Microplate Washers brochure, Tecan AG, Jul. 1997.

Genesis Series Robotic Sample Processors brochure, Tecan AG, Oct. 1997.

Genesis Robotic Microplate Processor brochure, Tecan AG, Nov. 1997.

Miniprep 75 Robotic Sample Processor brochure, Tecan AG Nov. 1997.

A Measure of brilliance, TR717 Microplate Luminometer brochure, Tropix, Inc. 1997.

Advanced Microplate Detection Systems brochure, Tecan AG, Feb. 1998.

The SPECTRA Family brochure, Tecan AG, Feb. 1998.

Assist Plate Handling Device brochure, Labsystems, May 1998.

Genesis Assay Workstation brochure, Tecan AG, Jul. 1998.

Genesis Logistics Workstation brochure, Tecan AG, Jul. 1998.

Polarion brochure, Tecan AG, Aug. 1998.

A Catalog of Reagents, Microplates and Accessories of Life Science Research, Book 2, Packard BioScience Company, Dec. 1998.

CytoFluor Fluorescence Multi–Well Plate Reader Brochure, PerSeptive Biosystems, 1998.
Setting the Standard, the HTS Compatibility Program brochure, Corning Incorporated, 1998.
Microplate Instrumentation catalogue, Labsystems, 1998.
Luc–Screen brochure, Tropix, Inc., 1998.
Nunc Products 1998–99 Catalog, Nalge Nunc International, 1998.
Advanced Microplate Washers, Tecan AG, Apr. 1999.
*Everything's Great When It Sits on a Chip*, Sinclair, *The Scientist*, vol. 13, No. 11, May 24, 1999.
*Assay Miniaturization for High–Throughput Screening*, Panfili, Sep. 1999.
CyBi™–Disk brochure, CyBio AG, Oct. 1999.
TWISTER™, Tecan's Automated Microplate Handler brochure, Tecan AG, Nov. 1999.
Magellan, Instrument Control and Data Analysis Software brochure, Tecan AG, Nov. 1999.
Handout Information, Tips and Tricks . . . Automated Liquid–Handling in the Microplate Format, CyBio AG, Nov. 1999.
Absorbance Readers brochure, Tecan AG, Dec. 1999.
ULTRA—The Solution for HTS and Assay Development brochure, Tecan Austria GmbH, Dec. 1999.
CyBi™–PlateSafe brochure, CyBio AG, May 2000.
CyBi™–Lumax 1,536 brochure, CyBio AG, May 2000.
CyBi™–Well 2000 brochure, CyBio AG, May 2000.
Packard BioScience Company Introduces the Fusion™ Universal Microplate Analyzer Press Release, Packard BioScience Company, Jun. 29, 2000.
Fusion™, Universal Microplate Analyzer, Packard BioScience Company, Aug. 2000.
ProxiPlate internet description page, Packard BioScience Company, printed Sep. 17, 2000.
Approaching the 2 $\mu$L to 10 $\mu$L Range: 384 Well Small Volume vs. 1536 Well Plates poster, Greiner Labortechnik, Sep. 2000.
SPECTRAmax® GEMINI XS brochure, Molecular Devices Corp., Jun. 2000.
SPECTRAmax® PLUS$^{384}$ brochure, Molecular Devices Corp., Jun. 2000.
Labcyte: Research and Clinical Instruments for Life Sciences brochure, Arlena Research LLC, Aug. 1, 2000.
CyBi™–Screen–Machine: One System–Many Solutions brochure, CyBio AG, 2000.
Reacti–Bind™ Metal Chelate High Binding CapacityPlates flyer, Pierce Chemical Company, 2000.
Reacti–Bind™ Metal Chelate Plates flyer, Pierce Chemical Company, 2000.
Reacti–Bind™ NeutrAvidin™ High Binding Capacity (HBC) Coated Plates Flyer, Pierce Chemical Company, 2000.
Reacti–Bind™ NeutrAvidin™ and Streptavidin Coated Plates Flyer, Pierce Chemical Company, 2000.
Reacti–Bind™ Streptavidin High Binding Capacity [HBC] Coated Plates Flyer, Pierce Chemical Company, 2000.
Nunc Life Science Discovery Products catalog, Nalge Nunc International Corporation, 2000.
FLIPR 384: Essential Technology for Drug Discovery brochure, Molecular Devices Corp., undated.
Acumen Explorer brochure, Acumen, undated.
FLUOstar Galaxy brochure, BMG Labtechnologies GmbH, undated.
LUMIstar Galaxy brochure, BMG Labtechnologies GmbH, undated.
NEPHELOstar brochure, BMG Labtechnologies GmbH, undated.
POLARstar Galaxy brochure, BMG Labtechnologies GmbH, undated.
POLARstar Galaxy flyer, BMG Labtechnologies GmbH, undated.
REMP 384 Tube Technology flyer, REMP (USA) Inc., undated.
REMP 96–Technology flyer, REMP (USA) Inc., undated.
Complete Sealing Solutions for Sample Integrity flyer, REMP (USA) Inc., undated.
High Throughput Screening brochure, Greiner America, Inc., undated.
PW 384 brochure, PanVera Corporation, undated.
Protein Kinase C (PKC) tech specs, PanVera Corporation, undated.

Fig. 9
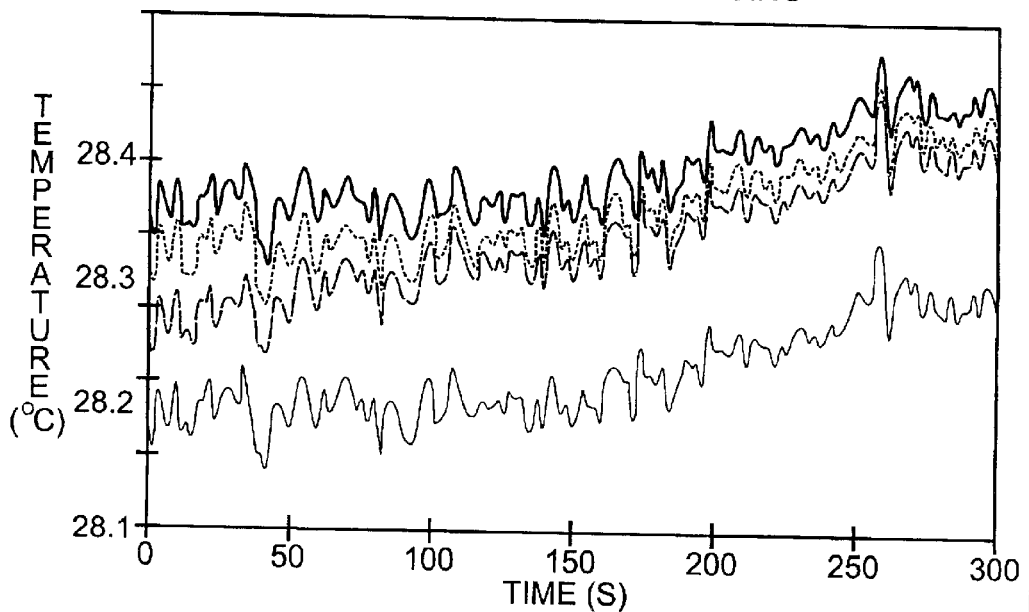
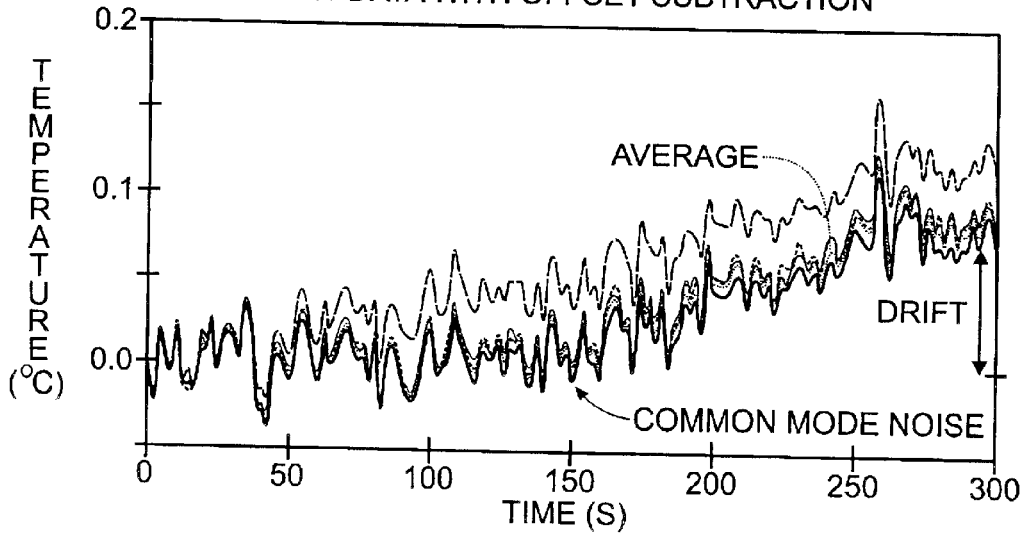

APPARATUS AND METHODS FOR INFRARED CALORIMETRIC MEASUREMENTS

CROSS-REFERENCES

This application is a continuation-in-part of the following U.S. patent applications: Ser. No. 09/777,363, filed Feb. 5, 2001; Ser. No. 09/777,368, filed Feb. 5, 2001; and Ser. No. 09/777,364, filed Feb. 5, 2001. These applications, in turn, are continuations of U.S. patent application Ser. No. 09/764,963, filed Jan. 17, 2001, which claims priority from the following U.S. provisional patent applications: Ser. No. 60/249,931, filed Nov. 17, 2000; and Ser. No. 60/256,852, filed Dec. 19, 2000. All of these patent applications are incorporated herein by reference in their entirety for all purposes.

RELATED REFERENCES

This application incorporates by reference in their entirety for all purposes the following publications: Kenneth R. Castleman, *Digital Image Processing* (1996); and Bob Sinclair, *Everything's Great When It Sits on a Chip: A Bright Future for DNA Arrays*, 13 THE SCIENTIST, May 24, 1999, at 18.

FIELD OF THE INVENTION

The invention relates to calorimetry. More particularly, the invention relates to apparatus and methods for performing calorimetry that use optical devices to detect thermal processes and/or multiwell sample plates to support samples for use with such optical devices.

BACKGROUND OF THE INVENTION

Thermodynamics has established the interrelationship between various forms of energy, including heat and work. Moreover, thermodynamics has quantified this interrelationship, showing, for example, that in chemical and physiological processes the difference between the energy of the products and the energy of the reactants is equal to the heat gained or lost by the system. In an "exothermic" process, this difference is negative, so that the process releases heat to the environment. Conversely, in an "endothermic" process, this difference is positive, so that the process absorbs heat from the environment. Thus, "calorimetry," or the measurement of heat production and/or heat transfer, can be used to determine if a chemical or physiological process is exothermic or endothermic and to estimate the energy produced or consumed.

The measurement of heat production and/or heat transfer in chemical and physiological processes can be quite complicated. Standardly, such measurements are made using a device known as a "bomb calorimeter." This device typically includes a sturdy steel container with a tight lid, immersed in a water bath and provided with electrical leads to detonate a reaction of interest inside the calorimeter. The heat evolved in the reaction is determined by measuring the increase in temperature of the water bath.

Unfortunately, bomb calorimeters are inadequate for the measurement of heat production and/or heat transfer in many areas of chemistry and physiology. For example, the study of processes involving uncommon and/or expensive components may require analysis of samples too small for bomb calorimetry. Similarly, the high-throughput screening of pharmaceutical drug candidate libraries for drug activity may require analysis of too many samples for bomb calorimetry.

The analysis of small samples is especially problematic due to their small heat capacities and large surface-to-volume ratios. Many chemical and physiological processes lead to very small changes in temperature (<0.05° C.), making their analysis susceptible to environmental contamination. In particular, whenever there is a temperature difference between a sample and the environment, heat can be exchanged between the sample and the environment, for example, by conduction, convection, and/or radiation, among others. Such heat exchange may quickly alter the temperature of a small sample and thereby obscure any temperature change associated with a reaction. Moreover, fluid samples such as those typically used in studies of chemical and physiological processes may initiate secondary reactions with the environment, such as evaporation. Evaporation, by definition, is an exchange of energy (moisture is added to the air, while chemical volume is reduced). This process takes place on the surface of the sample, where the sample is exposed to the environment, and so may be especially problematic for small samples due to their relatively large surface-to-volume ratios. Evaporation not only removes energy from the sample, contaminating the measurement, but also may increase measurement noise due to surface instability as the fluid phase changes to a gas phase.

SUMMARY OF THE INVENTION

The invention provides apparatus and methods for performing calorimetry. The apparatus include optical devices for detecting thermal processes and multiwell sample plates for supporting samples for use with such optical devices. The methods include measurement strategies and data processing techniques for reducing noise in measurements of thermal processes. The apparatus and methods may be particularly suitable for extracting thermal data from small differential measurements made using an infrared camera and for monitoring chemical and physiological processes.

BRIEF DESCRIPTION OF THE DRAWINGS

FIG. 9 is a graph showing the effects of offset subtraction on thermal data.

DEFINITIONS

Figure 1:
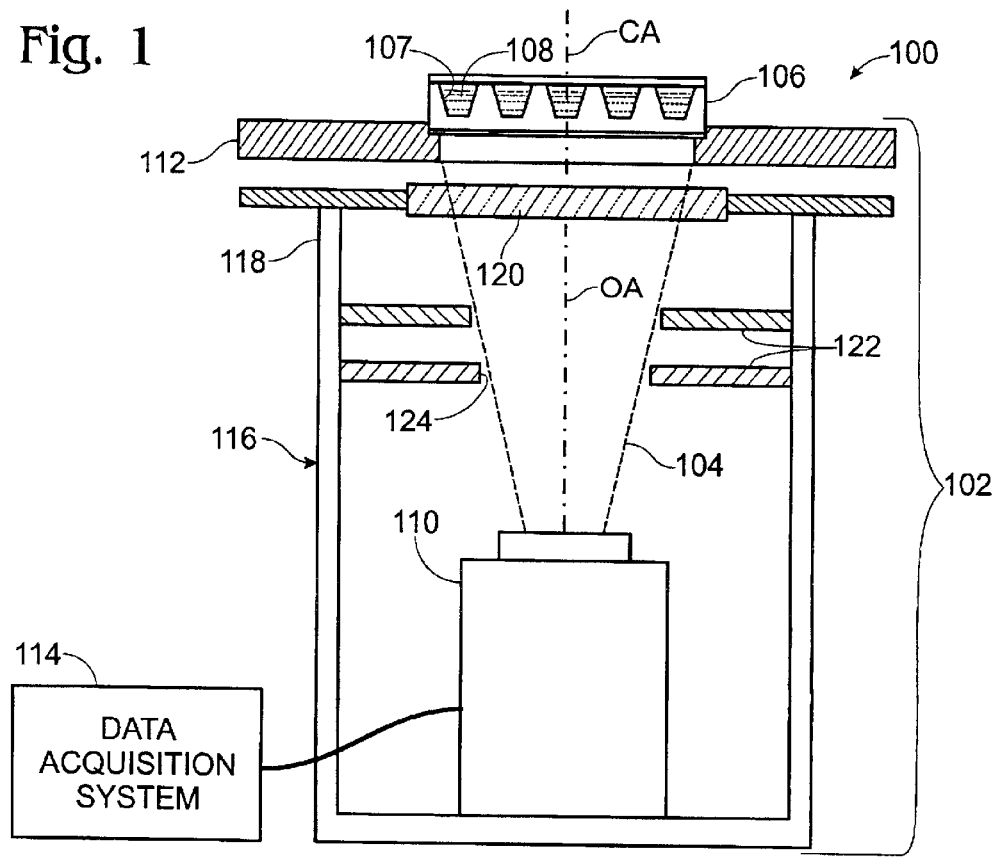
FIG. 1 is a partially schematic cross-sectional view of a system for detecting thermal processes.

Technical terms used in this application have the meanings that are commonly recognized by those skilled in the art. The following terms may have additional meanings, as described below:

Common-mode noise. Typically low-frequency (<1 Hz) noise caused when internal control loops, such as the servo on a cryogenic cooler, create response changes in the detector. In an infrared camera, these noise sources may be common to each sensor element and may be geometrically displaced across the sensor array. For example, at a given time, a thermal wave from the expansion of helium gas in a sensor cooler may cause slight gain changes in the sensor that cause a group of sensor elements in one geometric region of the array to respond differently, or out of phase with, another group of sensor elements in another region of the array. In most applications, common-mode noise is insignificant; however, in high-sensitivity (<0.05° C.) applications, common-mode noise may become a limiting factor.

Heat. A form of energy associated with the motion of atoms or molecules. Heat is capable of being transmitted by (1) conduction through solid and fluid media, (2) convection through fluid media, and (3) radiation through empty space.

Infrared (IR) radiation. Invisible electromagnetic radiation having wavelengths from about 700 nanometers, just longer than red in the visible spectrum, to about 1 millimeter, just shorter than microwave radiation. Infrared radiation includes (A) near IR (from about 700 nm to about 1,300 nm), (B) middle IR (from about 1,300 nm to about 3,000 nm), and (C) far or thermal IR (from about 3,000 nm to about 1 mm). Near and middle IR is infrared radiation that typically is caused by vibrations and low-level electronic transitions in molecules and that is only peripherally related to heat. In contrast, thermal IR (or thermal infrared radiation) is infrared radiation that is caused or produced by heat and that is emitted by an object in proportion to the temperature and emissivity of the object.

Radiosity. The radiation emanating from an object is determined by the following parameters: (1) emissivity, i.e., the amount of radiation the object emits, (2) reflectivity, i.e., the amount of externally derived radiation the object reflects, and (3) transmissivity, i.e., the amount of externally derived radiation the object transmits. For example, the thermal power P radiated by an object may be described by the equation $P=\epsilon \sigma A T^4$, where $\epsilon$ is the emissivity of the object, $\sigma$ is the Stefan-Boltzmann constant, A is the area of the object, and T is the temperature. Emissivity, reflectivity, and transmissivity are dimensionless parameters with values that range between 0 and 1. For a given material, the sum of these parameters should equal unity, so that each parameter is inversely correlated with the sum of the other parameters. A material with an opaque surface has a transmissivity of zero, so its emissivity equals one minus its reflectivity. Materials that radiate very well and absorb a large percentage of the radiation that strikes them have high emissivities.

Parasitic noise. Typically low-frequency (<0.1 Hz) noise caused by stray radiation incident on the detector from within the detector housing, creating an offset in output that results in measurement error. The stray radiation may be caused by slight temperature changes internal and/or external to the detector. In an infrared camera, the error may be geometrically displaced across the camera array, as determined by the efficiency of the cold shield for the camera sensor and the baffling within the Dewar. Most infrared cameras attempt to correct for parasitic noise using some form of internal calibration mechanism, such as a uniform-temperature shutter that periodically drops in front of the sensor to perform an offset compensation. These calibration mechanisms inherently interrupt measurements and can lead to measurement errors if the uniform-temperature shutter is not actually perfectly uniform in temperature. All infrared radiometers have some form of parasitic noise.

Spatial Noise. Typically lower-frequency (<60 Hz) highly nonlinear noise reflecting detector artifacts caused by variations in the manufacturing process, for example, during metal oxide vapor deposition (MOVD). In an infrared camera, these artifacts may cause slight differences in the gain or response characteristics, spectral characteristics, and/or stability characteristics of the various elements, columns, and/or rows of the sensor. Spatial noise may result in low-frequency noise or a drift component, which may still remain even after performing a calibration for pixel gain and offset in the camera.

Temporal noise. Typically high-frequency (>60 Hz) random noise caused by (radiated or conducted) electronic noise, A/D quantization, 1/f noise, microphonics, and/or a low electronic signal-to-noise ratio from the detector.

Thermal conductivity. The quantity of heat transmitted, due to a unit temperature gradient, in unit time under steady conditions in a direction normal to a surface of unit area, when the heat transfer is dependent only on the temperature gradient.

Thermodynamic noise. Noise caused by thermodynamic instabilities in a medium, such as a fluid-to-gas phase transition. Surface measurements of most fluids, including water, show significant instability due to thermodynamic noise caused by evaporation.

DETAILED DESCRIPTION

The invention provides apparatus and methods for performing calorimetry (or thermogenic analysis). The apparatus include optical devices for detecting thermal processes and multiwell sample plates for supporting samples for use with such optical devices. The methods include measurement strategies and data processing techniques for reducing noise in measurements of thermal processes. The apparatus and methods may be particularly suitable for (1) extracting thermal data from small differential measurements made using an infrared camera, and (2) for monitoring chemical and physiological processes.

FIG. 1 shows a system 100 for detecting thermal processes in accordance with aspects of the invention. The system includes an optical device 102 configured to detect thermal radiation 104 and a sample plate 106 having a sample well 107 configured to support a sample 108 for use with the optical device. The system may be used to monitor thermal processes in the sample or samples by detecting temperature changes correlated with heat production (e.g., from a chemical or physiological reaction) and/or heat transfer in the samples. This correlation may be performed using any suitable method, such as those described in the following U.S. provisional patent application, which is incorporated herein by reference: Ser. No. 60/256,852, filed Dec. 19, 2000. Moreover, this correlation may be used to examine reactions, as well as modulators such as agonists and/or inhibitors of the reactions. If there are multiple samples, the radiation transmitted from the samples may be detected sequentially from each sample, for example, by point reading, or simultaneously from some or all of the samples, for example, by image reading. The optical device may include a detector 110 such as an infrared optical sensor configured preferentially to detect thermal infrared radiation. The detector measures thermal energy radiated from a sample (or samples) supported by the sample plate and converts the measured energy to a signal such as an electrical signal that can be converted into a temperature, for example, using a blackbody or graybody approximation. In a preferred embodiment, the detector includes an imaging device such as an infrared focal plane array (FPA) configured to obtain a time-dependent series of two-dimensional infrared images of processes occurring in samples in a multiwell sample plate, permitting measurement of temperature and temperature changes in each process, as a function of time, geometrically across the plate. The series of images typically is collected at a preselected frequency (typically >1 Hz) for a preselected period significant relative to a characteristic time of any time-dependent process being monitored. The data subsequently may be processed and/or reported at the same and/or a lower frequency. The data may be used to monitor, screen, rank, and/or otherwise analyze thermal processes occurring in the sample. The thermal analysis may be used alone or together with other measurements to assess the presence, concentration, physical properties, and/or activity of a compound or compounds in the sample. Thus, the system provides a noncontact, noninvasive method for measuring thermal properties such as temperature, in contrast to bomb calorimeters, thermometers, and capacitive and resistive circuits.

The system and its components may be configured to improve the accuracy and/or sensitivity of thermal measurements, particularly thermal measurements involving small samples and/or small temperature changes. The optical device may be configured to reduce measurement errors associated with noise, such as common-mode, parasitic, spatial, temporal, and/or thermodynamic noise, among others. The sample plate may be configured to facilitate detection of thermal radiation through a surface of the plate and/or to reduce measurement-contaminating heat transfer between the samples and the environment (including other samples). The optical device and sample plate may together be configured to reduce noise associated with evaporation, for example, by using a bottom-read detector and a sample plate having an infrared-transmissive bottom surface and in some cases a cover.

The remainder of the Detailed Description is divided into four sections: (A) optical devices, (B) noise reduction, (C) sample holders, and (D) examples.

A. Optical Devices

The optical device generally comprises any device capable of preferentially detecting thermal infrared radiation and using the detected radiation to analyze thermal processes in a sample. The phrase "capable of preferentially detecting thermal infrared radiation" means that the device is configured and/or operated so that it detects more thermal infrared radiation than any other form of radiation (i.e., so that at least about half of the radiation detected is thermal infrared radiation). The phrase excludes any device that detects thermal infrared radiation only incidentally, as might occur in an optical device configured to detect visible light if thermal radiation leaked into the detector. The capability for preferentially detecting thermal infrared radiation may reflect use of one or more of the following mechanisms, among others: (A) use of spectral filters preferentially to "extract" thermal infrared radiating by blocking radiation other than thermal infrared radiation, including visible, near IR, or middle IR radiation, (B) use of detectors having enhanced sensitivity for thermal infrared radiation, and/or (C) postprocessing of a detector signal to reduce and/or compensate for any component of the signal not resulting from detection of thermal infrared radiation.

FIG. 1 shows an optical device 102 constructed in accordance with aspects of the invention in use as a part of a system 100 for detecting thermal processes. The device includes a detector 110 configured to detect thermal infrared radiation emitted by a sample, a stage 112 configured to support a sample in a sample holder for thermal analysis by the detector, and a processor 114 configured to analyze radiation detected by the detector. The detector and stage are positioned such that at least a portion of the thermal infrared radiation emitted by the sample is incident, indirectly or preferably directly, on the detector. This may be accomplished by ensuring that a central axis CA of the sample wells is aligned with an optical axis OA of the instrument prior to detection of thermal infrared radiation. Alignment simply means that the two axes are sufficiently close to parallel that radiation from a central portion of the sample well is detectable by the instrument. For example, in FIG. 1, the central axis of each sample well is aligned with the optical axis of the instrument. The detector may be positioned below the stage to form a "bottom-read" instrument, above the stage to form a "top-read" instrument, or in other positions to form other instruments. The instrument of FIG. 1 is a bottom-read instrument, and the instrument of FIG. 1 with components of the optical device 102 inverted and positioned above the stage is a top-read instrument.

The stage may be movable, so that samples may be deposited at a first position, moved to a second position for fluid dispensing, moved to a third position for thermal equilibration, moved to a fourth position for thermal detection, and moved to a fifth position for pickup. These positions may be the same or different, and any given position (except the detection position) may be present or absent. The stage may move sample holders translationally and/or rotationally, among others.

The sample generally comprises any object or system of objects intended for thermal analysis. The sample may include compounds, mixtures, surfaces, solutions, emulsions, suspensions, cell cultures, fermentation cultures, cells, tissues, secretions, and/or derivatives and/or extracts thereof. The sample also may include the contents of a single sample site, or several sample sites, depending on the assay.

The detector generally comprises any device for preferentially detecting thermal infrared radiation and converting the detected radiation into a signal representative of the detected radiation. A preferred detector is an imaging detector, such as an infrared camera, that is capable of simultaneously viewing part or all of a sample holder. Further aspects of the detector are described below in Section B.

The stage generally comprises any mechanism for supporting a sample in a sample holder at an examination site for thermal analysis by the device. A preferred stage is a transporter capable of moving the sample holder vertically and/or horizontally between the examination site and one or more transfer sites where the sample holder can be loaded onto and/or unloaded from the stage.

The processor generally comprises any mechanism for analyzing the signal from the detector, for example, to conduct a thermal analysis. The analysis may include conversion of a signal representative of intensity and/or wavelength into a signal representative of temperature and/or differential temperature, among others. The analysis also may include performing calculations to reduce noise and/or to facilitate data reporting, as described below. The processor may be intrinsic to the detector, extrinsic to the detector, or both. Further aspects of the processor are described below in Section B.

The optical device also may include a housing 116 to support and protect the detector. The housing may include, among others, an optics tube 118, an infrared-transmissive window 120, and/or a baffle 122 having an aperture 124. The optics tube may support the detector and/or components of the housing, such as the window and baffles. The optics tube also may reduce the amount of unintended thermal infrared radiation entering the detector. The window may permit thermal infrared radiation to enter the housing for detection, while also permitting the housing to be sealed to reduce contamination and/or (partially) evacuated to reduce absorption and/or scattering of thermal radiation prior to detection. The window may include a portion formed of zinc selenide (ZnSe) and/or polyethylene, among others. The baffles may block stray thermal infrared radiation. The optical device may be configured to shield the sample from incident radiation to reduce the proportion of the sample signal arising from transmission, reflection, and/or photoluminescence from the sample.

The optical device also may include a data output mechanism such as a view screen or printer for reporting results of any thermal analysis. Data generally may be reported using any suitable method, physical and/or electronic, digital and/or analog, and static and/or time varying, among others. Suitable methods include tables, graphs, and/or images, among others. Data may include temperatures and/or temperature differentials, among others, at a fixed time or as a function of time. Further aspects of the data output mechanism including suitable software are described below in Section D.

B. Noise Reduction

Noise is almost invariably a problem in measurements of thermal processes. However, noise may be especially problematic in measurements of thermal processes involving small samples and/or small temperature changes, where even minor noise can obscure or overwhelm any temperature change associated with the thermal process.

The effects of noise on measurements of thermal processes can be reduced using noise reduction techniques. Noise reduction involves identifying sources of noise (e.g., measurement noise, camera noise, etc.), and then developing methods for reducing or eliminating the noise and/or its effects. Unfortunately, thermal detectors such as infrared cameras are susceptible to several types of noise, including common-mode, parasitic, spatial, and/or temporal noise, among others. In addition, fluid samples are susceptible to other types of noise, including thermodynamic noise, which is caused by thermodynamic transformations, such as evaporation, in which the sample changes from a fluid to a gas. These and other forms of noise are described above, under Definitions. Thus, noise reduction in measurements of thermal processes may be facilitated by the application of one or more different methods, and/or by the repeated application of the same and/or related methods.

The present "state of the art" for infrared, radiometric cameras defines measurement performance in terms of noise-related parameters, specifically, accuracy and sensitivity. Here, accuracy is a relative absence of error or mistake, and sensitivity is an ability to detect or measure an input, especially a weak input. The sensitivity of infrared cameras normally is quantified in terms of noise equivalent temperature difference (NETD), which is the RMS noise/response at a given temperature, f#, and operating frequency (normally 30° C., f/1, and 60 Hz). NETD typically is the limiting factor in determining measurement sensitivity. A typical, state-of-the-art, high-performance infrared camera, such as the FLIR SC3000, using Quantum Well (QWIP) sensor technology, specifies an absolute accuracy of about 2° C. and a sensitivity (NETD) of about 0.03° C. Unfortunately, this sensitivity may be inadequate in measurements of small temperature changes.

The invention provides methods for reducing noise and/or enhancing accuracy and/or sensitivity in thermal measurements, particularly measurements involving small samples and/or small temperature changes. These methods may improve upon the previous state-of-the-art sensitivity described above, potentially providing sensitivities of <0.1° C. or even <0.01° C. and RMS noise levels of <0.05° C. or even <0.005° C., at least when the methods are used on data collected with preferred sample holders.

The methods may be implemented using any suitable apparatus, such as those described above in Section A. These apparatus may include one or more processors associated intrinsically and/or extrinsically with the optical device and incorporating instructions for and capable of carrying out the functions specified by the methods. The processor(s) may perform during signal acquisition by the optical device, for example, so that the most recent image is a processed image formed as a running average of the actual most recent image and a preselected number of preceding images. Alternatively, or in addition, the processor(s) may perform after signal acquisition, for example, in a central processing unit used to run the apparatus and/or experiments conducted using the apparatus.

The methods may be performed using any suitable analysis mode, including continuous (analog) and/or discrete (digital) modes, and point-reading and/or imaging modes. Thus, the signal may be collected using an analog camera (such as a video camera) and/or a digital camera (such as a charge-coupled device (CCD) camera), and/or using an analog and/or a photon-counting point-reading detector (such as a photomultiplier tube, photodiode, etc.). In an exemplary embodiment, signals are collected in imaging mode, and analog signals (if any) are converted to digital signals prior to and/or during analysis. A digital signal typically takes the form of one or more digital images, which typically comprise two- or three-dimensional quantized functions that have been generated by optical means, sampled using a defined spatial pattern (such as an equally spaced rectangular grid), and represented using a defined presentation scale (such as an equal level gray scale or a pseudocolor scale). A two-dimensional digital image T may be represented as an M×N matrix of values $T_{ij}$ associated with spatial positions i and j. A series of two-dimensional digital images (such as a time series) may be represented as an M×N×k matrix of values $T_{ij}(k)$ by further associating a time index k with each spatial value $T_{ij}$.

The methods may involve point operations and/or area operations, among others. Here, a point operation is an operation that modifies data on a point-by-point (e.g., pixel-by-pixel) basis depending only on the value and/or location of the data point. In contrast, an area operation is an operation that modifies data on a point-by-point basis depending at least in part on the value and/or location of points in the neighborhood of the data point. The methods may involve replacing a given number of data points or images with an equal number of potentially modified data points or images. Alternatively, or in addition, the methods may involve replacing two or more data points or images with a smaller number of data points or images.

The invention may involve application of one or more of the following techniques, among others, as described below: (1) low-pass filtering, (2) temporal averaging, (3) spatial averaging, (4) reference calibration, (5) offset subtraction, and/or (6) bottom reading.

1. Low-pass Filtering

Low-pass filtering generally comprises any method for reducing or eliminating high-frequency temporal and/or spatial noise by blocking or otherwise suppressing frequencies above a certain "cutoff frequency" while passing or otherwise promoting frequencies below the cutoff frequency. Thus, to reduce high-frequency "temporal noise" in thermal images, data may be collected at a relatively high frame rate and passed through a low-pass time-domain filter to cut out the high-frequency noise. In an exemplary embodiment, full-field radiometric data are collected using an infrared camera as described above at a 60-Hz frame rate and passed through a low-pass filter internal to the camera electronics to yield filtered data corresponding to a lower frame rate. Suitable low-pass filters are described in Kenneth R. Castleman, *Digital Image Processing* (1996), which is incorporated herein by reference. In particular, suitable low-pass filters include (1) simple low-pass filters, such as the box filter, triangular filter, and high-frequency cutoff filter, and (2) more complex low-pass filters, such as the Gaussian low-pass filter. A preferred low-pass filter includes a frame-average as described below in which the most recent image represents a frame-average of the most recent image with one, three, seven, or fifteen of the most recent preceding images, among others.

2. Temporal Averaging

Temporal averaging generally comprises any method for summarizing or representing the general significance of a set of unequal values of a quantity or function sampled at different times, such as determination of a mean, mode, or median value, among others. In an exemplary embodiment, temporal averaging involves application of frame-averaging, among others. Here, frame-averaging may be used to reduce any residual high-frequency temporal noise remaining after application of a low-pass filter.

Frame-averaging generally comprises averaging (or otherwise smoothing) data over a series of frames. For example, a pixelated function T may be frame-averaged over N frames by summing the product of the value of the function $T_{ij}$ and a corresponding weighting factor $W_{ij}$ in each frame k, and then dividing the sum by the sum of the weighting factors:

$$\langle T_{ij} \rangle_{FA} = \frac{\sum_{k=1}^{N} W_{ij}(k) T_{ij}(k)}{\sum_{k=1}^{N} W_{ij}(k)} \xrightarrow{W_{ij}=1 \forall ij} \frac{1}{N} \sum_{k=1}^{N} T_{ij}(k) \qquad (1)$$

Here, $\langle \rangle_{FA}$ denotes frame-averaging. The weighting factors all may be equal (for example, they all may be equal to one), or some or all of the weighting factors may have different values, depending on the algorithm. The frame-averaged frame may be used to replace an input frame, typically a middle or final frame, in the series of N frames used to construct the average. The number of frames will be unchanged (absent edge effects) if each frame in a series of frames is replaced with a frame-averaged frame. In contrast, the number of frames will be reduced if two or more frames are replaced with a single frame-averaged frame.

The preferred number N of frames to use in the frame-average is determined by competing factors. Generally, it is better to use a larger number of frames because frame-averaging typically reduces high-frequency random temporal noise by the square root of the number of frames averaged. However, the overall time corresponding to the number of frames used in the average should be small relative to the time scale of thermal changes in the system to avoid averaging frames that differ due to actual differences in the temperature of the sample rather than due merely to noise. In the data presented below in Section D, the optimum number of frames for frame-averaging was between about 4 and 16.

Frame-averaging may be performed simultaneously and/or sequentially for different samples, and/or for measurement and reference areas.

3. Spatial Averaging

Spatial averaging generally comprises any method for summarizing or representing the general significance of a set of unequal values of a quantity or function sampled at different positions, such as determination of a mean, mode, or median value, among others. Data may be spatially averaged to return a reduced number of (average) values or a single (average) value for each area as a function of time. For example, a pixelated function T may be area-averaged for a particular frame k by summing over some or all of the M pixels ij in a given area A of a frame the product of the value of the function $T_{ij}$ and a corresponding weighting factor $W_{ij}$, and then dividing the sum by the sum of the weight factors:

$$\langle T \rangle_{AA}(k) = \frac{\sum_{i,j \in A} W_{ij}(k) T_{ij}(k)}{\sum_{i,j \in A} W_{ij}(k)} \xrightarrow{W_{ij}(k)=1 \forall ij} \frac{1}{M} \sum_{i,j \in A} T_{ij}(k) \qquad (2)$$

Here, $\langle T \rangle_{AA}$ denotes area-averaging. The weighting factors all may be equal (for example, they all may be equal to one), or some or all of the weighting factors may have different values, depending on the algorithm. Thus, in a sample holder having 96 sample wells each having a measurement area and a reference area, area averaging may be used to reduce the data set to as few as 96 measurement values and 96 reference values by independently averaging pixel values over all or part of each measurement and reference area. The measurement and reference areas may be distinguished using application software implemented in the processor. Area averaging typically involves >4 pixel elements and preferably involves >9 pixel elements. Area averaging may reduce the effects of geometric, spatial noise common to most FPA detectors. Such noise may reflect defective or nonlinear detector elements and/or slight differences in amplifier characteristics. In some applications, area averages may be computed as median values or mode values, as appropriate, instead of mean values.

The following table shows an exemplary algorithm for area averaging data from contiguous measurement and reference regions. The number of data points used in the average and the number of averages reported by region may be selected according to any criterion or criteria. Generally, most or all of the data points unambiguously ascribable to one or the other region but not both will be used in the average, and, generally, one average will be reported for each region.

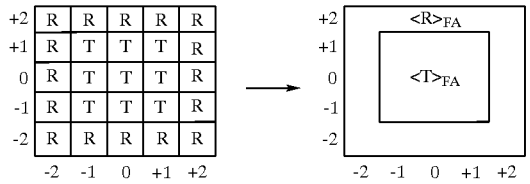

4. Reference Calibration

Data may be calibrated using a reference standard, such as an adjacent local (e.g., perimeter) reference standard, for example, by subtracting a reference value from a corresponding measurement value to return a differential measurement for each sample well as a function of time.

$$T_{RC} = T_{Meas} - T_{Ref} \quad (3)$$

Here, the measured and reference values may be properties of the thermal radiation detected from the measurement and reference regions, respectively, such as intensities, or they may be quantifies derived from such properties, such as temperatures. The method may be applied pixel-by-pixel or area-by-area, among others. Subtracting reference values from measurement values may reduce or eliminate common-mode noise, internal drift, and/or parasitic noise local to the region of the detector array used in the measurements. These noise sources have a tendency to be geometrically dispersed across the sample holder or sample wells, so that other noise-reduction techniques, such as single-point reference or Fourier transform characterization and subtraction have limited success. These other methods have a tendency to amplify noise where it shifts out of phase relative to adjacent areas, whereas the local reference compensates for geometric shifting.

5. Offset Subtraction

Data may be adjusted by subtracting one or more offsets from each measurement.

$$T_{OS} = T - T_{Offset} \quad (4)$$

The offset may be used to set the initial-time differential measurements for each sample well at t (time)=0, so that there is a common starting point from which to measure changes in temperature. Offset subtraction effectively creates a zero reference at the beginning of the experiment and adjusts the difference in temperature between the measurement region and associated reference region to zero. Adjusting the offset to zero may compensate for field nonuniformity resulting from camera drift prior to the start of data collection.

In some applications, data may be adjusted further by multiplication (or, equivalently, division) by a suitable scaling factor.

6. Bottom Reading

Reading through the bottom of an infrared-transmissive sample well may reduce thermodynamic noise created at the interface of dry air and the sample. In particular, evaporation at sample surfaces exposed to dry air may create a saturated gas layer adjacent the sample surface. This layer may be opaque or nearly opaque to the thermal detector and show significant instability (measured to be >0.05° C.). Measurement noise created by evaporation may be fivefold or more greater than measurement noise associated with reading through the bottom of the sample well or from an independent black body reference. Additionally, evaporation at the surface may lower the surface temperatures measured by the camera by as much as 2° C. This 2° C. difference is a heat sink for the reaction being measured. Bottom reading allows the top surface of the sample well to be sealed so that the space above the sample becomes saturated with moisture, reducing evaporation noise and heat loss.

The application of these noise-reduction methods generally is quite flexible. For example, each method generally may be applied separately, alone or in combination with any number of other methods. Moreover, each method generally may be applied in any order.

C. Sample Holders

The sample holder (or, equivalently, the sample substrate or sample plate) generally comprises any substrate or material capable of supporting a sample or samples for thermal analysis. The sample holder preferably is capable of supporting a plurality of samples at discrete (i.e., individually distinct) sample sites. Suitable sample holders may include microplates, PCR plates, microarrays, chromatography plates, and microscope slides, among others, where microplate wells and biochip array sites comprise assay or measurement sites. Exemplary microplates are described below in detail. These and similar sample holders such as PCR plates generally keep each portion of each sample from mixing with each portion of each other sample. Exemplary microarrays (or, equivalently, biochips) are described in detail in Bob Sinclair, *Everything's Great When It Sits on a Chip: A Bright Future for DNA Arrays*, 13 THE SCIENTIST, May 24, 1999, at 18. These and similar sample holders generally keep at least a portion of each sample from mixing with at least a portion of each other sample, for example, by adhering the molecules of interest such as nucleic acids or proteins to specific array sites while allowing the solvent and any associated dissolved or suspended species to move between sites.

The sample holder may include a thermal isolation structure disposed between the sample wells to reduce thermal transfer between the wells and the environment and thus between adjacent wells. The thermal isolation structure may include a thermal buffer, thermal barrier, and/or isolation well, among others, as described below. The thermal isolation structure may be composed at least in part of a different material than the sample wells. The thermal isolation structure may substantially surround a central or optical axis of each sample well, isolating the wells without obstructing transmission of thermal infrared radiation along the central axis. The thermal isolation structure also may be disposed such that any straight line below a plane formed by the tops of the sample wells connecting a portion of one sample well to a portion of an adjacent sample well intersects the isolation structure.

The sample holder also may include an insert member defining an array of sample wells and a support member having a thermal isolation framework in a configuration corresponding to the array of sample wells. The sample wells each may have a central axis, and the insert may engage the support member such that each sample well is thermally isolated from adjacent sample wells without obstructing the transmission of thermal infrared radiation along the central axis. The thermal isolation framework may include a thermal buffer, thermal barrier, and/or isolation well, among others, as described below.

The sample holder also may include an insert having a plurality of sample wells, and a thermal isolation member for supporting the insert so that each sample well can be precisely positioned along an optical path, where the thermal isolation member provides a thermally controlled thermal reference surface adjacent each well as viewed along the optical path. The reference surface may define an aperture that frames the associated optical path.

A preferred sample holder is configured as a microplate having a frame and a plurality of sample wells disposed in the frame for holding a corresponding plurality of samples for analysis. This format may combine small-volume samples and a high-density holder, permitting automated analysis of large numbers of samples. This format also may be configured to reduce unintended heat exchange between the samples and the environment (including between the sample and other samples) and/or to permit an optical detector to measure thermal infrared radiation transmitted through a surface of the sample holder.

The sample holder may include one or more of the following features, among others:

1. Thin Surface

A sample well having at least one surface having a thickness of less than about 0.005 inches, and preferably less than about 0.001 inches, and most preferably less than about 0.0005 inches. A thin surface may be important for at least two reasons: (1) increased infrared transmissivity, and (2) decreased thermal conductivity. These two criteria preferably may be met using a single material, such as a polymeric polyethylene blend having a high infrared transmissivity (e.g., greater than about 50% or about 80%) and a low thermal conductivity (e.g., less than about 1 W/m-K or about 0.6 W/m-K).

A thin (i.e., reduced-thickness) surface may increase transmissivity. A thin surface may be less likely to absorb thermal energy being radiated by the sample due to its shorter path length and more likely to have an outer (i.e., non-sample-contacting) surface at the same temperature as the sample, facilitating calorimetric analysis through the surface. A preferred thin surface has a high transmissivity (e.g., >80%) for thermal infrared radiation, particularly thermal infrared radiation having wavelengths between about 3 and 5 micrometers and between about 7 and 14 micrometers. (These wavelength ranges may be especially useful in thermal imaging, because they correspond to minima in atmospheric absorption.) A thin more transmissive surface preferably is located at least at the bottom of the sample well to permit detection from the underside of the sample holder using a bottom-read analyzer. The surface may be substantially (e.g., optically) flat to reduce optical aberrations during analysis through the surface.

A thin (i.e., reduced-thickness) surface also may decrease thermal conductivity. There are three primary mechanisms for heat transfer in the plate: conduction, convection, and radiation. Typically, conduction is the most significant mechanism, and radiation is the least significant mechanism. Conduction may be described by the equation $P=KA\nabla T$, where K is the thermal conductivity, A is the surface area, and $\nabla T$ is the temperature gradient. Thus, reducing surface area may reduce conduction. A primary path for conduction is through the walls of the sample well to contact points on the associated frame. This path may be reduced using thin-walled sample wells. Moreover, because the thermal conductivity of air (~0.02 W/m-K) is less than that of the preferred well material (0.6 W/m-K), it is important to use the air as much as possible for a conduction path. Thus, the wells hold heat much like a thermos. Finally, the thermal capacitance of a thin material is lower, so that there is less change in temperature due to the initial $\Delta T$ in the system. In particular, the material may be selected such that the thermal mass of the sample wells is no more than about half the thermal mass of an aqueous sample positioned in the sample well, even when the sample well is completely full. A thin less conductive surface preferably is located at least at the sides of the sample well.

2. Thermal Buffer

A thermal buffer disposed between the sample wells to resist thermal transfer between sample wells, or between the environment and the sample wells. The thermal buffer generally comprises any mechanism for resisting a change in temperature. In this sense, the thermal buffer resembles a pH buffer, which resists a change in pH when an acid or base is added to a solution by binding to the added species, or an electrical capacitor, which resists a change in voltage by storing or releasing charge. The thermal buffer may be used to buffer (or keep relatively constant) the temperature of any structure adjacent the sample well, such as the trapped volume described below. The thermal buffer may include a structure having a high thermal mass (or heat capacity), which can absorb heat without undergoing a significant change in temperature. This high thermal mass structure may, for example, have a substantially higher thermal mass (or heat capacity) than the sample wells and/or corresponding samples, for example, three, five, or even ten times higher. The high thermal mass structure may include a metal such as aluminum and/or a high thermal capacitance plastic, among others.

3. Thermal Barrier

A thermal barrier disposed between the sample wells to block thermal transfer between sample wells. The thermal barrier generally comprises any mechanism for blocking the transfer of heat into or out of the sample wells or the vicinity of the sample wells, such as an adjacent trapped volume. The thermal barrier may include a material having a low emissivity and/or a high reflectivity for infrared radiation. For example, the thermal barrier may include a material that reflects at least about half of the infrared radiation that otherwise would be incident upon surfaces of the sample well. Generally, emissivity and reflectivity are inversely related; thus, shiny, metallic materials tend to have low emissivities and high reflectivities, whereas matte, dark-colored materials tend to have high emissivities and low reflectivities. In a preferred embodiment, the thermal barrier includes a material having a reflectivity of at least about 0.8 and an emissivity of at most about 0.2.

4. Double-walled Sample Wells

A double-walled sample well, formed, for example, by positioning a sample well in a corresponding isolation well. In a preferred embodiment, a plurality of isolation wells are disposed in a frame, a corresponding plurality of sample wells are disposed in the isolation wells, and none of the sample or isolation wells is in fluid contact with another of the sample or isolation wells. The double-walled wells may include a trapped volume formed between an outer surface of the sample wells and an inner surface of the corresponding isolation wells, further reducing thermal transfer to and from samples positioned in the sample wells. The trapped volume may enclose air and/or an inert gas, and/or be partially or fully evacuated relative to standard atmospheric pressure. The trapped volume also may enclose or be lined along its perimeter with a thermal barrier, i.e., a material having a low emissivity and/or a high reflectivity for infrared radiation to reduce radiation thermal transfer to and from the sample well.

5. Plural Optically Transmissive Surfaces

A plurality of optically transmissive surfaces, at least one associated with the frame and at least one associated with the sample well, where the surfaces are configured so that an optical reader can detect electromagnetic radiation such as infrared radiation transmitted from a sample through both the optically transmissive surface of the corresponding sample well and the optically transmissive surface of the frame. For example, a plurality of optically transmissive surfaces may be formed by corresponding surfaces of a sample well and isolation well in a double-walled well, as described above.

6. Measurement and Reference Regions

A combination of a measurement region and a reference region. The measurement region may be a portion of a sample well, and the reference region may be an adjacent portion of the frame, isolated from the sample well, particularly a high-thermal-mass and/or high emissivity (>0.5 and preferably >0.8) surface portion capable of acting as a blackbody or graybody reference. The reference region may be composed at least in part of a different material than the sample wells and may include a metal such as aluminum. The reference region(s) may be disposed adjacent (e.g., about or between) the sample wells, so that each measurement region is near a corresponding reference region, reducing artifacts that reflect temperature drift across the sample plate. Thus, an M×N array of measurement regions might be complemented by an M×N of reference regions disposed about the measurement regions, or an (M−1)×(N−1) array of reference regions disposed between the measurement regions. The reference region may be configured as a ring or annulus distributed about or adjacent a perimeter of the sample well and/or about and preferably symmetrically about a central axis of the sample well. The reference region may be positioned about or above the top of a corresponding sample well, and/or about or below a corresponding sample well. The reference regions and the corresponding sample wells may be separated by a gap such as an air gap along a line connecting each portion of the thermal reference regions and the corresponding sample wells to reduce heat transfer between the sample wells and the thermal reference regions. Thermal characteristics of the measurement region may be calibrated using thermal characteristics of the reference region, for example, by subtracting the reference characteristic from the measurement characteristic. This calibration may reduce geometrically dispersed common-mode noise, including the effects of internal parasitic radiation and camera drift. The use of dedicated reference regions may free up all of the sample wells for data analysis, because none of the wells needs to be used as a reference well.

7. Consumable Sample Well Inserts

A combination of a reusable frame and a consumable sample well insert (or a set of consumable sample well inserts) configured to fit within or mate with the frame. The combination may facilitate reuse of portions of the sample holder that are expensive, such as the thermal buffer and/or thermal barrier. The combination also may facilitate disposal of portions of the sample holder that contact the sample by reducing the amount of such materials that must be discarded. The combination may be constructed so that the insert is substantially supported by the frame yet substantially thermally insulated or isolated from the frame. The frame and the sample wells may be composed of the same or preferably different materials. Here, consumable may be defined as more likely to be discarded than reused, typically because it is more convenient and/or less expensive to be discarded than reused. For example, a consumable sample well insert may obviate the need to clean sample wells between samples.

8. Cover

A cover configured for use with the sample holder. The cover generally comprises any mechanism for covering the sample holder, or a portion of the sample holder, to reduce contamination of the samples and/or to reduce evaporation from the samples (e.g., by reducing exposure to dry air and/or convective air currents), among others. The cover generally may be formed of any suitable material, such as a rigid plastic and/or a thin layer of oil or other less evaporative material layered over the sample. The cover may be infrared transmissive, so that samples may be analyzed through the cover using a top-read analyzer. The cover may be configured to touch the top surface of the sample. Alternatively, the cover may be configured to leave an air gap between the top surface and the cover, particularly a small air gap that may quickly saturate with fluid vapor after fluid samples are positioned in the wells and before reactant or catalyst are delivered to reduce evaporative cooling during analysis. Generally, evaporation may be reduced by reducing the size of the air gap, for example, by using shallow wells and/or by substantially filling the wells (for example, until the samples occupy at least about half or even about eight-tenths or nine-tenths of the volume of the sample wells). Alternatively, or in addition, evaporation may be reduced by increasing the humidity of the air adjacent the sample well or sample holder. The cover may include an aperture so that a fluid delivery system such as a pipette can pierce the cover and deliver reactant fluids.

D. EXAMPLES

The following examples describe without limitation further aspects of the invention. These examples show that thermal cross talk between sample wells can be reduced by thermally isolating the sample wells and that thermal resolution and the accuracy and sensitivity of thermal measurements can be enhanced by reducing noise, including common-mode, parasitic, spatial, temporal, and/or thermodynamic noise, among others. Additional examples including color drawings showing pseudocolor methods for displaying thermal imaging data are described in the following U.S. provisional patent application, which is incorporated herein by reference: Ser. No. 60/256,852, filed Dec. 19, 2000.

Example 1

This example describes a preferred sample holder for use in measurements of thermal processes, including chemical and physiological processes.

Figure 2:
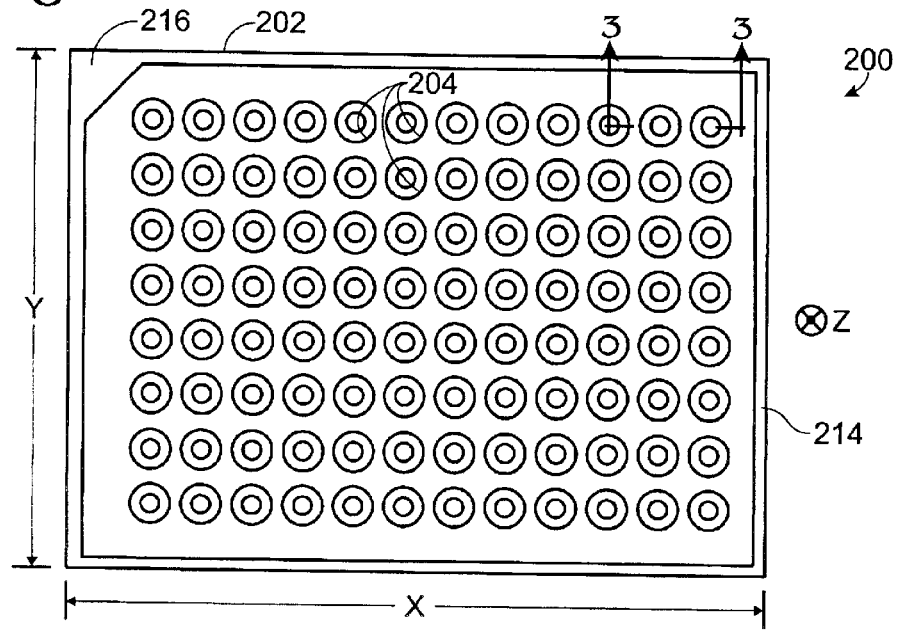
FIG. 2 is a top view of a multiwell sample holder for use with an optical device for detecting thermal processes.
Figure 3:
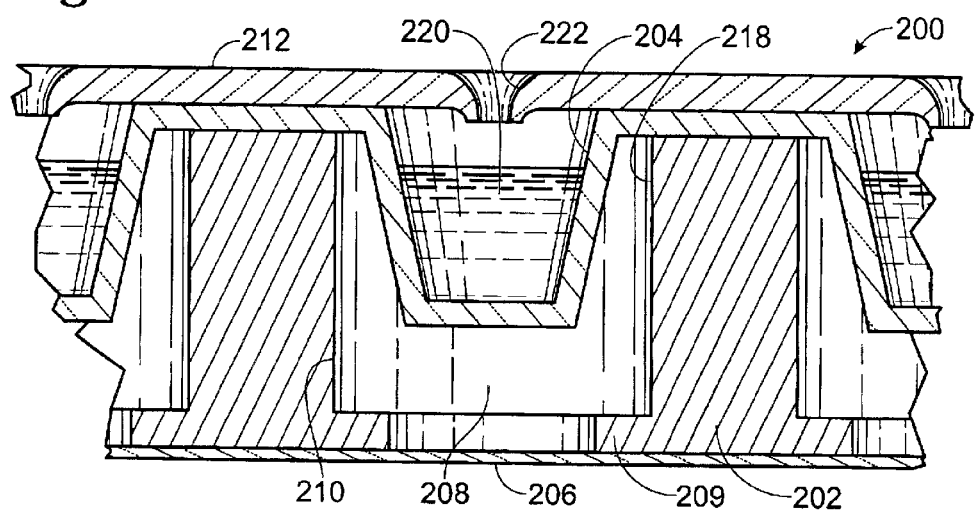
FIG. 3 is a cross-sectional view of the multiwell sample holder of FIG. 2, taken generally alone line 3—3 in FIG. 2.

FIGS. 2 and 3 show a sample holder 200 constructed in accordance with aspects of the invention. The sample holder includes a high thermal mass frame or base 202, a plurality of sample wells 204 and a corresponding plurality of windows 206, trapped volumes 208, reference regions 209, and opaque coatings 210, and a cover 212.

Frame 202 is the main structural component of sample holder 200. The frame generally may be sized and shaped as desired, for both convenience and utility. Frame 202 is sized and shaped to form a microplate, enabling the sample holder to be used with standard microplate equipment, such as handlers, washers, and/or readers, among others. A preferred frame is substantially rectangular, with a major dimension X of about 125–130 mm, a minor dimension Y of about 80–90 mm, and a height Z of about 5–15 mm, although other dimensions are possible. Frame 202 may include a base 214 configured to facilitate handling and/or stacking, a notch 216 configured to facilitate receiving the cover, and/or a plurality of apertures 218 configured to receive and support a corresponding plurality of sample wells. The apertures provide clearance around the sample wells, creating an air gap that may provide thermal isolation between the base and the sample well. The apertures may be formed using any suitable method, including machining and/or casting the frame to include the apertures. The inner surface of each aperture may be polished and/or lined with an opaque (i.e., low transmissivity) coating 210 such as AlSiO or gold to reflect infrared radiation and thus to form a thermal barrier to heat conduction to and from the sample wells. In this embodiment, adjacent sample wells may be separated by two thermal barriers and a portion of the frame disposed between the two thermal barriers. The apertures and/or the sample wells may be tapered, such that the separation between the sample wells and the walls of the corresponding apertures increases from the top to the bottom of the sample wells, further reducing conduction between the sample wells and the walls of the apertures.

The frame generally may be constructed of any suitable material. For example, frame 202 is constructed using a material having a high thermal mass (heat capacity) and high thermal conductivity, such as aluminum and/or other metals. Preferred materials such as aluminum may reduce the time required for thermal stabilization within the test chamber while being sturdy enough for repeated, rugged use. In particular, a high thermal mass base (and/or an adjacent structure) may function as a thermal buffer, helping to maintain a constant temperature around sample wells positioned in apertures 218.

Sample wells 204 are used to support and separate samples 220 for calorimetric analysis. These sample wells may vary in size, shape, number, and arrangement, generally as desired, as long as the wells fit in the frame, and more particularly fit within the corresponding apertures in the frame. Exemplary sizes range between about 1 $\mu$L and about 500 $\mu$L, and more preferably between about 1 $\mu$L and about 200 $\mu$L. Exemplary shapes include cones, frustums of cones, cylinders, and parallelepipeds, among others. Exemplary numbers include 96, 384, 864, 1536, 3456, and 9600, among others. Exemplary arrangements include rectangular and hexagonal arrays, among others. Three preferred sample-well configurations that will fit as rectangular arrays within a microplate-sized frame are listed in the following table:

| Number of Wells | Arrangement of Wells | Pitch (mm) Between Wells | Density (/mm$^2$) of Wells |
|---|---|---|---|
| 96 | 8 × 12 | 9 | 1/81 |
| 384 | 16 × 24 | 4.5 | 4/81 |
| 1536 | 32 × 48 | 2.25 | 16/81 |

Here, pitch is the center-to-center well-to-well spacing, and density is the number of wells per unit area. In a preferred embodiment, the frame will include a similarly spaced array of apertures for receiving the sample wells. A preferred configuration includes 96 frustoconical wells organized in an 8×12 rectangular array. Here, frustoconical refers to a well shape having conical sides and a flat bottom, as shown in FIG. 3.

The sample wells may be formed as cups that may be inserted into the frame to hold a sample of calorimetric analysis, permitting an analyzer to measure temperature changes in the sample, for example, resulting from chemical or physiological processes. In this way, a single frame may be used to support cups of different sizes and shapes, so long as the cup (or cups) will fit within the corresponding apertures. The bottom surface 221 of the cup may be flat and/or particularly thin in areas from which infrared measurements are collected. A flat surface may serve to reduce optical distortion and control reflections coming from the surface. A thin surface may enhance infrared transmission, because infrared properties generally are proportional to material thickness. A thin surface also may help to ensure that the outer surface remains at or very close to the temperature of the fluid.

The cup inserts may be formed individually or joined to form a sheet or sheets of cups for use in the frame. Individual cups and small sheets of cups generally provide greater flexibility, permitting cups to be mixed and matched (e.g., according to size, shape, and/or infrared transmission properties, among others) within a single plate. Large sheets of cups provide greater structural stability and convenience, permitting many cups to be changed at once. As mentioned above, cup inserts generally are configured so that a single cup resides within a single aperture in the supporting frame. However, cup inserts also may be configured so that two or more cups reside within a single aperture, permitting a single frame to support cups at two or more significantly different sizes and/or densities.

Figure 4:
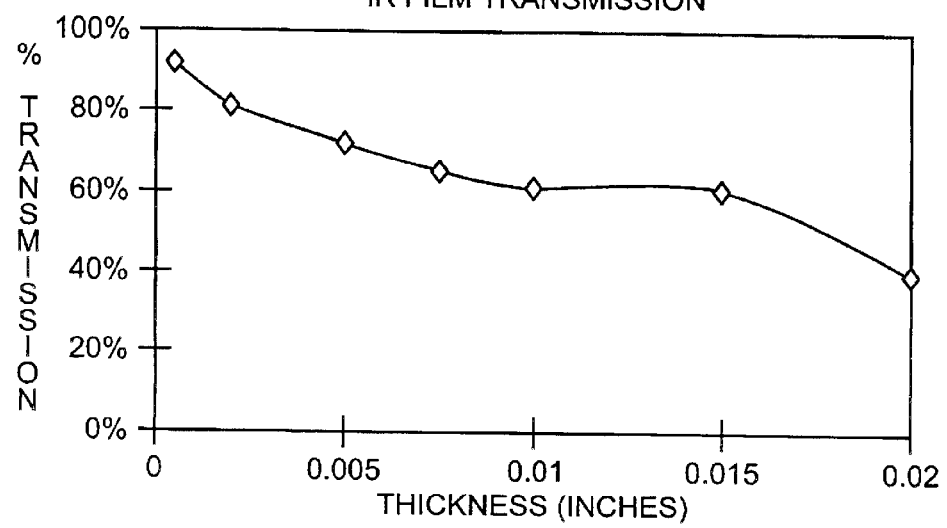
FIG. 4 is a graph showing the infrared transmissivity of a preferred sample well material as a function of the thickness of the material.

The material properties of the cups are important for thermal isolation and infrared transmissivity. FIG. 4 shows the infrared transmissivity of a preferred cup material as a function of material thickness. This preferred material is an infrared-transmissive (polymeric) polyethylene blend sold under the trademark Poly IR 2™ by Fresnel Technologies. The material has a high infrared transmissivity that increases nonlinearly with decreasing material thickness, showing a significant increase for thicknesses below about 0.001 inches. Moreover, the material has a low coefficient of thermal conductivity (~0.6 watts/meter-kelvin), which is about $\frac{1}{10}$ the thermal conductivity of most other infrared-transmitting materials, including Zn, Se, and Ge. In addition, the material has a low thermal mass, so it should quickly assume the temperature of the sample. The low thermal mass of the cup combined with its low thermal conductivity and insulation from the base reduce heat loss to the environment. The infrared transmission properties of the material allow the detector to measure the temperature of the fluid through the cup with less than 10% thermal contribution from the cup. Further aspects of the preferred sample well material are described in the following U.S. provisional patent application, which is incorporated herein by reference: Ser. No. 60/256,852, filed Dec. 19, 2000.

Window 206 is an environmental seal between the sample well and the detector (located below the sample holder) when the sample holder is used with a bottom-read analyzer. The window may be formed of an infrared-transmissive membrane material selected to enhance infrared transmission within the spectral sensitivity band of the camera. A preferred material is zinc selenide, which provides >97% transmission to the bottom surface of the sample well.

Trapped volume 208 is formed between inner surfaces of frame 202, sample well 204, and window 206. The high thermal mass frame that surrounds the sample well acts as a capacitor to maintain a constant temperature within the trapped volume, which typically contains air. The inner surfaces of the frame may be lined with an opaque coating, as described above.

Reference region 209 is a source of a reference signal for use in reference calibrations to reduce common-mode and parasitic noise, among others, as described above. Generally, each sample well includes a measurement region and a corresponding reference region. The measurement region generally comprises a portion of the sample or sample well, such as an infrared transmissive bottom portion of the sample well for use with bottom-read instruments. The reference region may comprise an adjacent portion of the frame, such as an annular donut-shaped portion formed around a perimeter and/or central axis of the measurement region. Here, the reference region is positioned at an end of a support member formed by portions of the frame disposed between the sample wells. The thermal mass of the thermal reference region and associated support member may be at least about the same as or greater than the thermal mass of the corresponding sample well and/or sample. The reference region may be formed of a high thermal mass and/or high (>0.8) emissivity material such as a metal that acts as an isolated, blackbody reference. The thermal reference region may include a substantially flat emissive reference surface, where the emissive surface is substantially parallel to a flat portion of the bottom of the sample well and/or where the emissive surface is within a factor of ten of the area of a flat portion of the bottom of the sample well.

Cover 212 provides a mechanism for covering the sample holder, or a portion of the sample holder, to protect samples from evaporation and/or reduce the likelihood and amount of evaporation. Cover 212 generally will leave a small air gap between the sample and the cover that may saturate with fluid vapor to reduce evaporation. Cover includes an aperture 222 so that a fluid delivery system such as a pipette can pierce the cover and deliver reactant fluids.

Example 2

Figure 5:
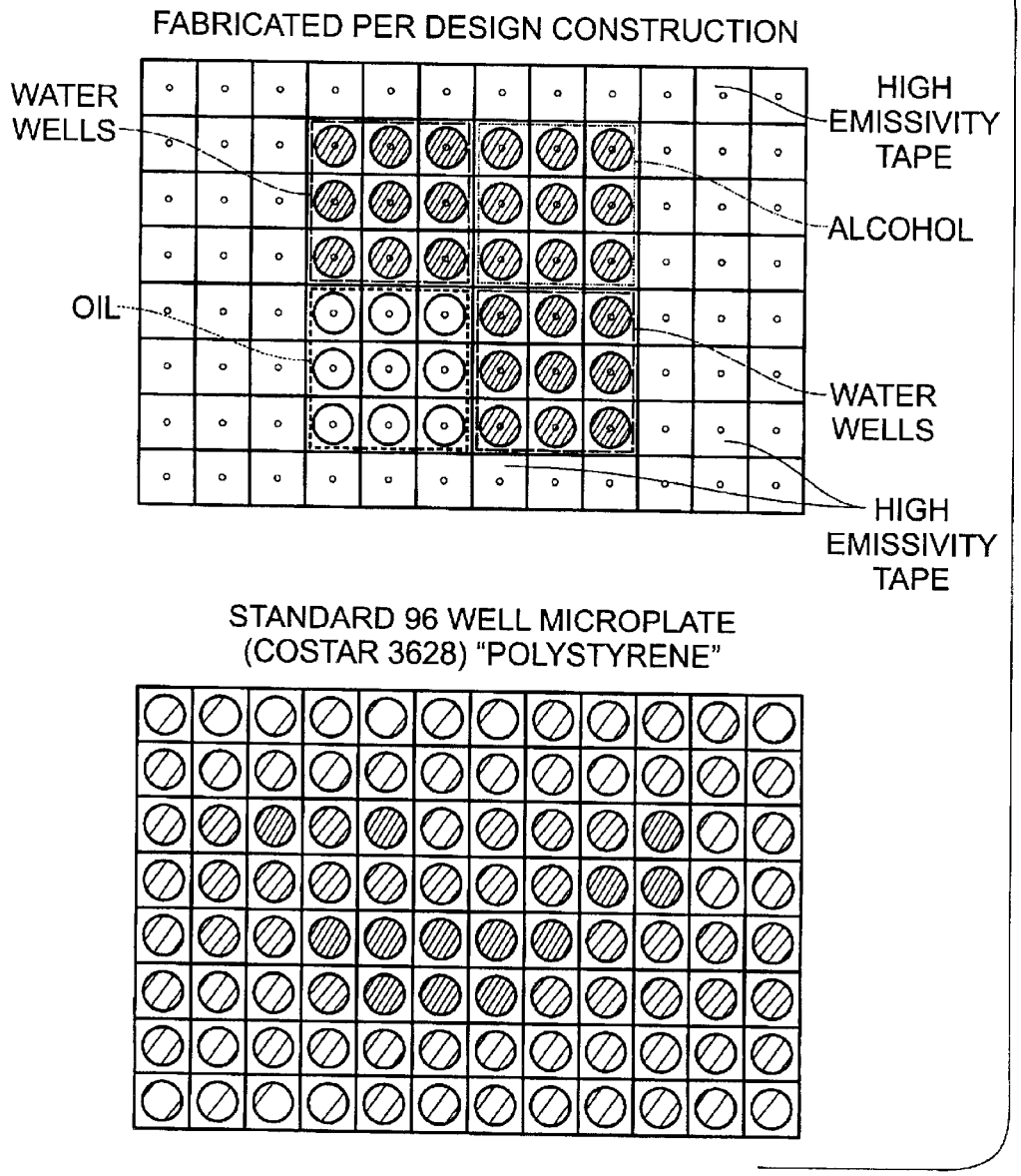
FIG. 5 is a pseudo-color image showing the extent and effect of thermal cross talk in sample wells in (A) the microplate of FIGS. 2 and 3 and (B) a standard commercial microplate.

FIG. 5 shows results from an experiment designed to measure thermal cross talk caused by heat conduction through the sample plate. The experiment was performed using a top-read thermal-imaging apparatus fitted with a quantum well (QWIP) infrared radiometer from FLIR Systems. The figure shows thermal images of two plates containing a fluid that evaporates when in contact with dry ambient air. Here, relative temperature is denoted by shading, where samples with relatively high temperatures have increased shading, and samples with relatively low temperatures have reduced shading. Plate 1 (left) is fabricated using a thin polymer insert and a high thermal mass base, as shown in FIGS. 2 and 3. Plate 2 (right) is a standard commercially available 96-well microplate fabricated from a polystyrene polymer (Costar 3628). The thermal images show that plate 1 provides significantly better thermal isolation than plate 2. In particular, the wells in plate 1 are insulated from the surrounding base material, reducing thermal "cross talk" between adjacent wells, whereas the wells in plate 2 are poorly insulated, enhancing thermal "cross talk" and leading to significant thermal gradients across the plate.

Example 3

This example describes results of an experiment designed to test the effects of evaporation on the apparent temperature of samples positioned in wells in a multiwell plate.

The experiment was performed using the top-read thermal-imaging apparatus and low cross-talk multiwell plate of Example 2. In these experiments, sets of adjacent wells were filled with fluids having various evaporation characteristics or else were covered with a high-emissivity tape, as shown below.

| T | T | T | T | T | T | T | T | T | T | T | T |
|---|---|---|---|---|---|---|---|---|---|---|---|
| T | T | T | W | W | W | A | A | A | T | T | T |
| T | T | T | W | W | W | A | A | A | T | T | T |
| T | T | T | W | W | W | A | A | A | T | T | T |
| T | T | T | O | O | O | W | W | W | T | T | T |
| T | T | T | O | O | O | W | W | W | T | T | T |
| T | T | T | O | O | O | W | W | W | T | T | T |
| T | T | T | T | T | T | T | T | T | T | T | T |

Here, A=alcohol, W=water, O=mineral oil, and T=tape. Alcohol and water are prone to evaporation, whereas mineral oil and tape are not. The apparent temperature in each well was measured at fixed intervals during a 15-minute period.

The data show that evaporation affects the apparent temperature of the samples. Specifically, the apparent temperature of wells containing water or alcohol was about 27° C., whereas the apparent temperature of wells containing mineral oil or tape was about 29° C., or about 2° C. warmer. Apparently, evaporation of water and alcohol cools the layer of gas above these fluids, leading to lower measured temperatures.

The data also show that evaporation affects the apparent temperature stability of the samples. Specifically, after compensating for common-mode noise, wells containing water or alcohol showed about 0.1° C. peak-to-peak (PTP) temperature variations, whereas wells containing mineral oil or tape showed about 0.01° C. PTP temperature variations, or about one-tenth as large. Thus, evaporation may preclude accurate measurement of small thermal processes within a well containing a fluid prone to evaporation, at least if measured from above the well. Conversely, reducing evaporation may improve thermal signal and permit a more accurate measurement of thermal reactions within the well.

Example 4

This example describes results of an experiment designed to determine whether temporal noise was caused by evaporation at the surface of the fluid and whether temporal noise could be controlled by reading the fluid through a transparent film.

The experiment was performed using the top-read thermal-imaging apparatus and multiwell plate of Examples 2 and 3. However, here, each well was filled with water. Moreover, a first set of data was collected as above, with the water exposed to ambient air, and a second set of data was collecting after placing a thin (~0.0005-inch thick) infrared-transparent film (Poly IR II) over the wells, in direct contact with the water to simulate a bottom-read design. The temperature in each well was again measured at fixed intervals during a 15-minute period.

Figure 6:
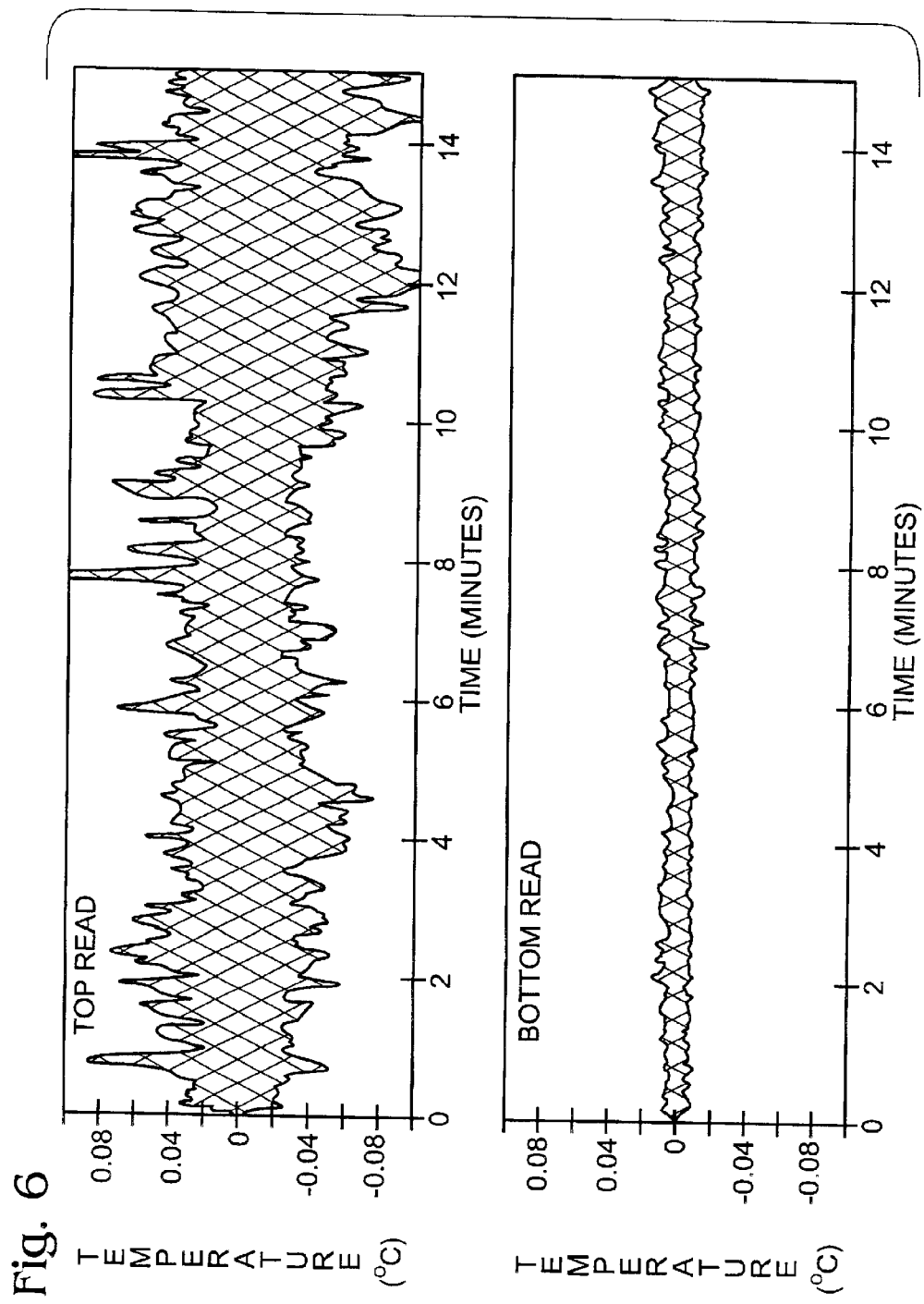
FIG. 6 is a graph showing noise envelopes associated with measurements of sample temperature taken from the (A) top and (B) bottom of a sample well after application of common-mode noise subtraction, area averaging, and frame-averaging. The noise envelope associated with the top-read data is significantly larger than the noise envelope associated with the bottom-read data due to evaporation.

FIG. 6A ("top read") shows the range of measured temperatures as a function of time, after subtraction of common-mode noise, reading from the surface of the exposed water.

The data show significant thermodynamic noise, resulting from evaporation at the surface of the water, with temperature variations of greater than about 0.1° C. (PTP). This noise level would make it very difficult to derive small temperature changes resulting from chemical or physiological processes beneath the surface.

FIG. 6B ("bottom read") shows the range of measured temperatures as a function of time, after subtraction of common-mode noise, reading through the infrared-transparent film. The data show significantly reduced temporal noise, with temperature variations of less than about 0.025° C. (PTP). In this case, the film reduces or prevents evaporative cooling because the fluid no is longer exposed to dry air. This reduction in evaporative cooling reduces noise in the measurement, which allows the system to record significantly smaller changes in temperature. This measurement technique, particularly when combined with the novel multiwell plate design of FIGS. 2 and 3, allows accurate recording of small subsurface processes taking place in the sample well, improving measurement resolution by about fourfold.

Example 5

Figure 7:
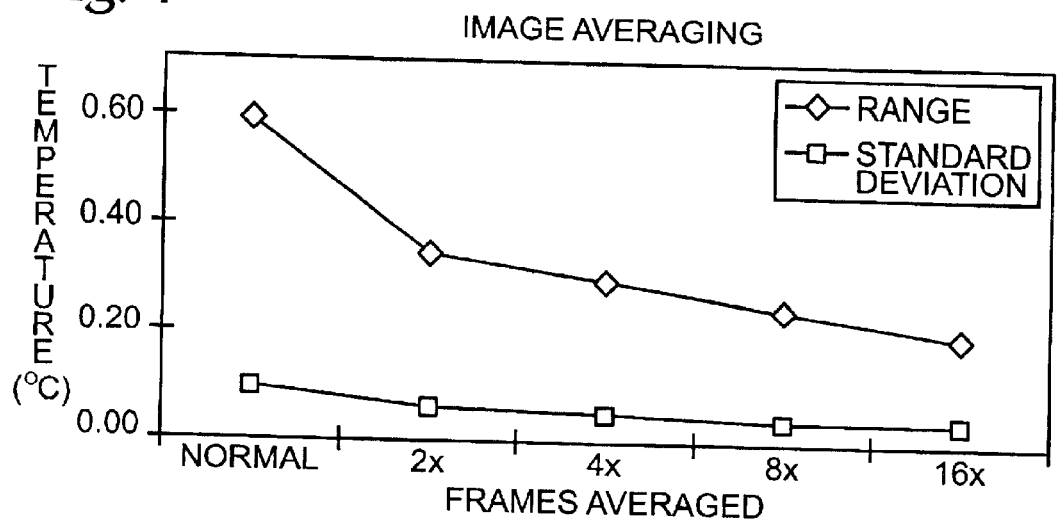
FIG. 7 is a graph showing the size of the noise envelope as a function of the number of frames average in an image-averaging experiment.

FIG. 7 shows results of an experiment designed to determine the preferred number of frames to average in the frame-averaging noise-reduction technique. The experiment was performed using top-read thermal-imaging apparatus and low cross-talk multiwell plate of Examples 2–4. The experiments show the noise level at several areas of the multiwell plate, averaged over 0, 2, 4, 8, and 16 frames at 60 Hz. The following chart summarizes the data for selected areas within the image:

|  | Normal | 2× Frames | 4× Frames | 8× Frames | 16× Frames |
|---|---|---|---|---|---|
| Max (bit counts) | 10656.00 | 10632.00 | 10632.00 | 10616.00 | 10600.00 |
| Min (bit counts) | 10560.00 | 10576.00 | 10584.00 | 10576.00 | 10568.00 |
| Avg (bit counts) | 10611.17 | 10604.05 | 10610.28 | 10592.24 | 10582.40 |
| Range (Kelvin) | 0.60 | 0.35 | 0.30 | 0.25 | 0.20 |
| Std Dev (Kelvin) | 0.10 | 0.07 | 0.05 | 0.04 | 0.04 |

Values are in 14 bit units. The "std dev" row is the root-mean-squared (RMS) noise of a uniform target after application of frame-averaging.

Example 6

Figure 8:
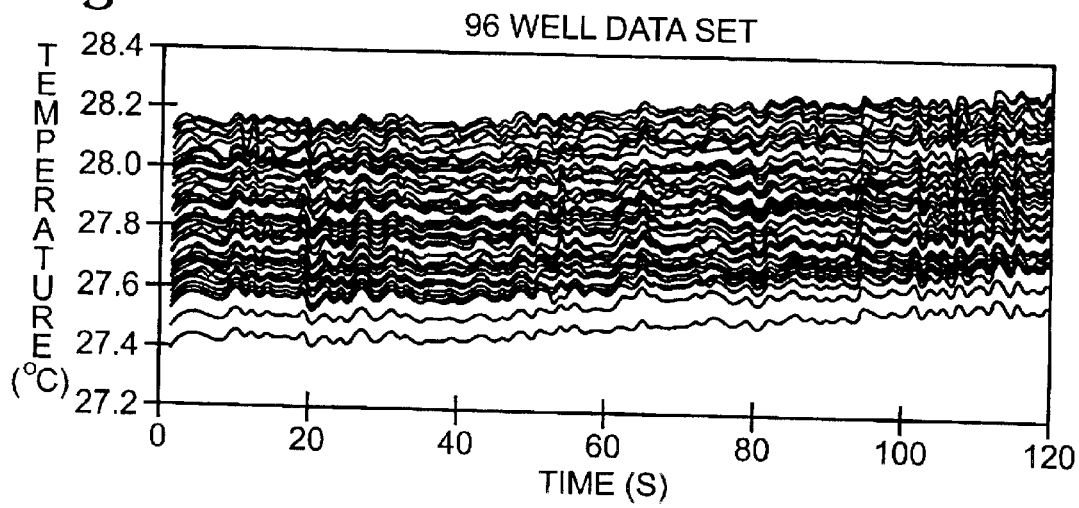
FIG. 8 is a graph showing the effects of common-mode noise and drift on thermal data collected using an infrared camera.

FIG. 8 shows results of an experiment designed to determine the level of common-mode noise typical of an infrared camera. The experiments were performed using the apparatus and plate of Examples 2–5. The figure shows a typical raw data set after frame-averaging (high-frequency noise reduction) and area averaging, but before common-mode noise reduction and offset subtraction.

Example 7

FIG. 9 shows results of an experiment designed to assess the ability of offset subtraction to extract data for a 135-$\mu$W reaction in a multiwell plate. The experiments were performed using the apparatus and plate of Examples 2–6.

FIG. 9A shows raw data for an experiment using four sample wells in which one well received a "sample" comprising a constant 135-$\mu$W input, while the other wells received a benign (i.e., non-reactive) sample. The data show the average temperature in the measurement region as a function of time, after image averaging is applied.

FIG. 9B shows the same data after offset subtraction, which adjusts the data so that each measurement starts at zero at time zero. There is a residual common-mode noise of approximately 0.05° C. PTP, after offset subtraction. This common-mode noise may be out of phase and may shift depending on the geometric position of the cell, as shown in FIG. 8.

Example 8

Figure 10:
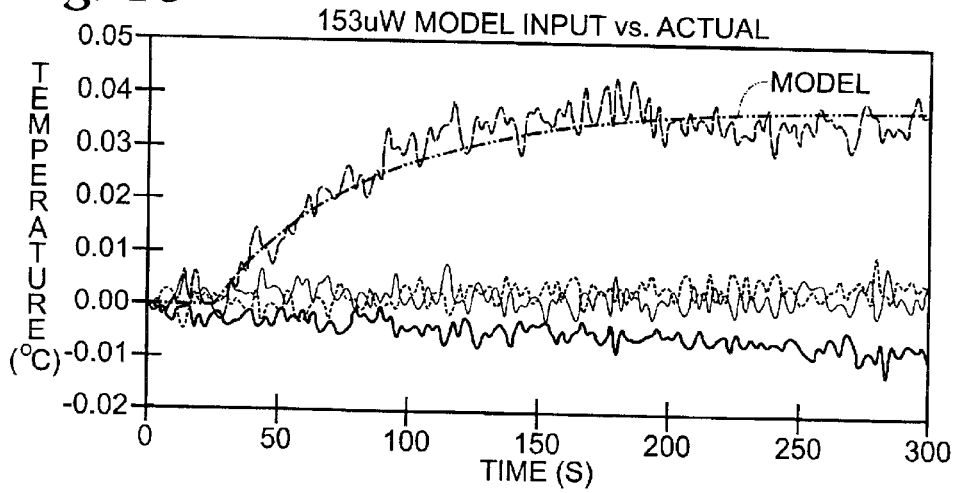
FIG. 10 is a graph showing the effects of removing common-mode noise on thermal data.

FIG. 10 shows results of an experiment designed to assess the ability of offset subtraction and the reduction of common-mode noise using a reference region local to the measurement region to extract data for the 135-$\mu$W reaction of Example 7 and FIG. 9. The reduction of common-mode noise reduces the noise level for the benign wells to an RMS level of about 0.004° C. The presence and thermal profile of the 135-$\mu$W reaction is clearly visible relative to the benign wells. The data compare favorably to a thermal model that calculates the theoretical effect of a 135-$\mu$W input on a sample holder having the same fluid volume. Without using the measurement and noise-reduction methods described here, the reaction resulting from a 135-$\mu$W input could not be detected using an infrared camera.

Example 9

This example describes software for performing and/or evaluating calorimetric measurements.

Figure 11:
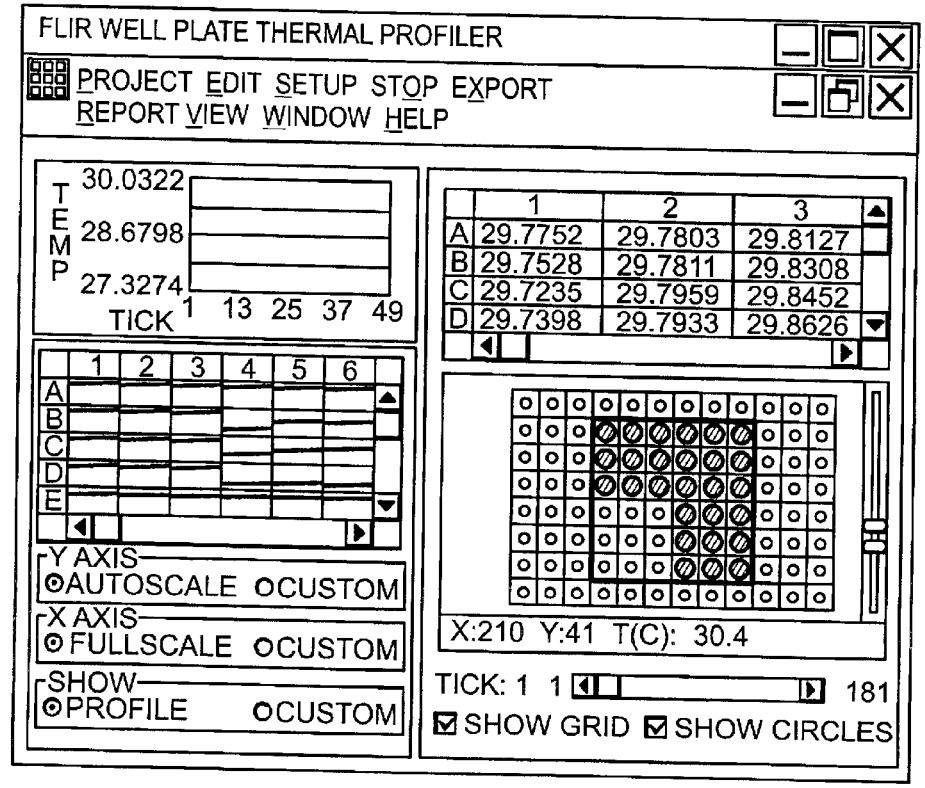
FIG. 11 is a software screen for use in the display of thermal data, including temperatures and temperature differentials.

FIG. 11 shows a software screen for the display of thermal data. The software screen may include one or more data presentation fields. These fields may be used to present data using any suitable form, including tables, graphs, and pseudo-images, among others. The fields may include a single display that includes or summarizes data from multiple samples, and/or multiple displays that each include or summarize data from one or a subset of the multiple samples. If there are multiple displays, they may be arranged in a manner representative of the layout of the corresponding samples, such as an 8×12 array of mini-graphs corresponding to the 8×12 array of samples in a standard 96-well microplate. The data displayed in the software screens may include a characteristic of the thermal radiation detected, such as the amount, intensity, and/or spectrum of the radiation. The data also may include a computed and/or processed quantity related to a characteristic of the thermal radiation detected, such as a temperature and/or a signal processed to reduce noise. The data also may include kinetic data, such as temperature versus time (denoted "tick"). The software screen also may include software switches for selecting the scale of the display, for example, X-axis and Y-axis scales for graphical data and color schemes for pseudocolor images, among others.

Figure 12:
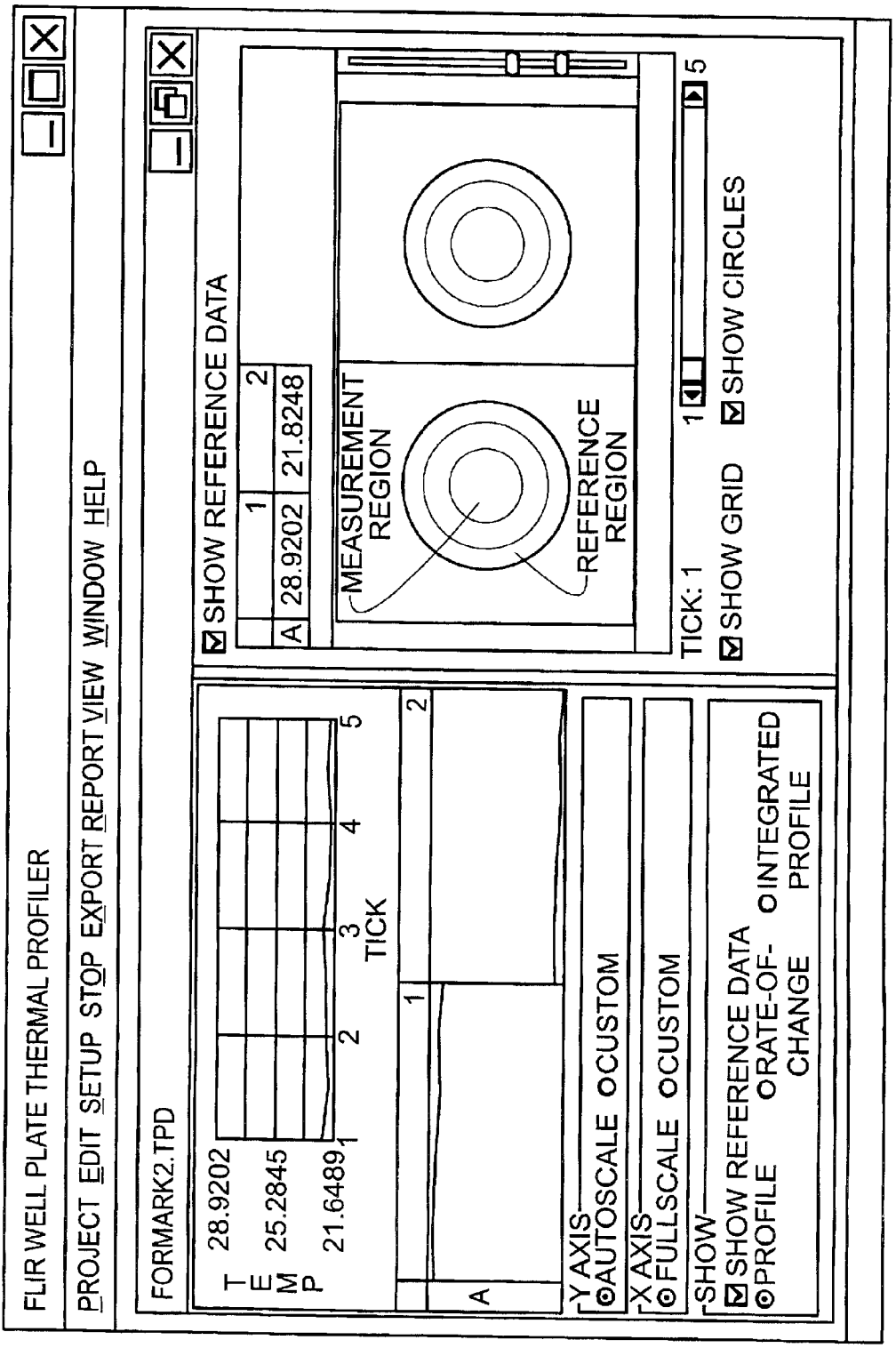
FIG. 12 is a software screen for use in the collection and/or analysis of data from measurement and reference regions.
Figure 13:
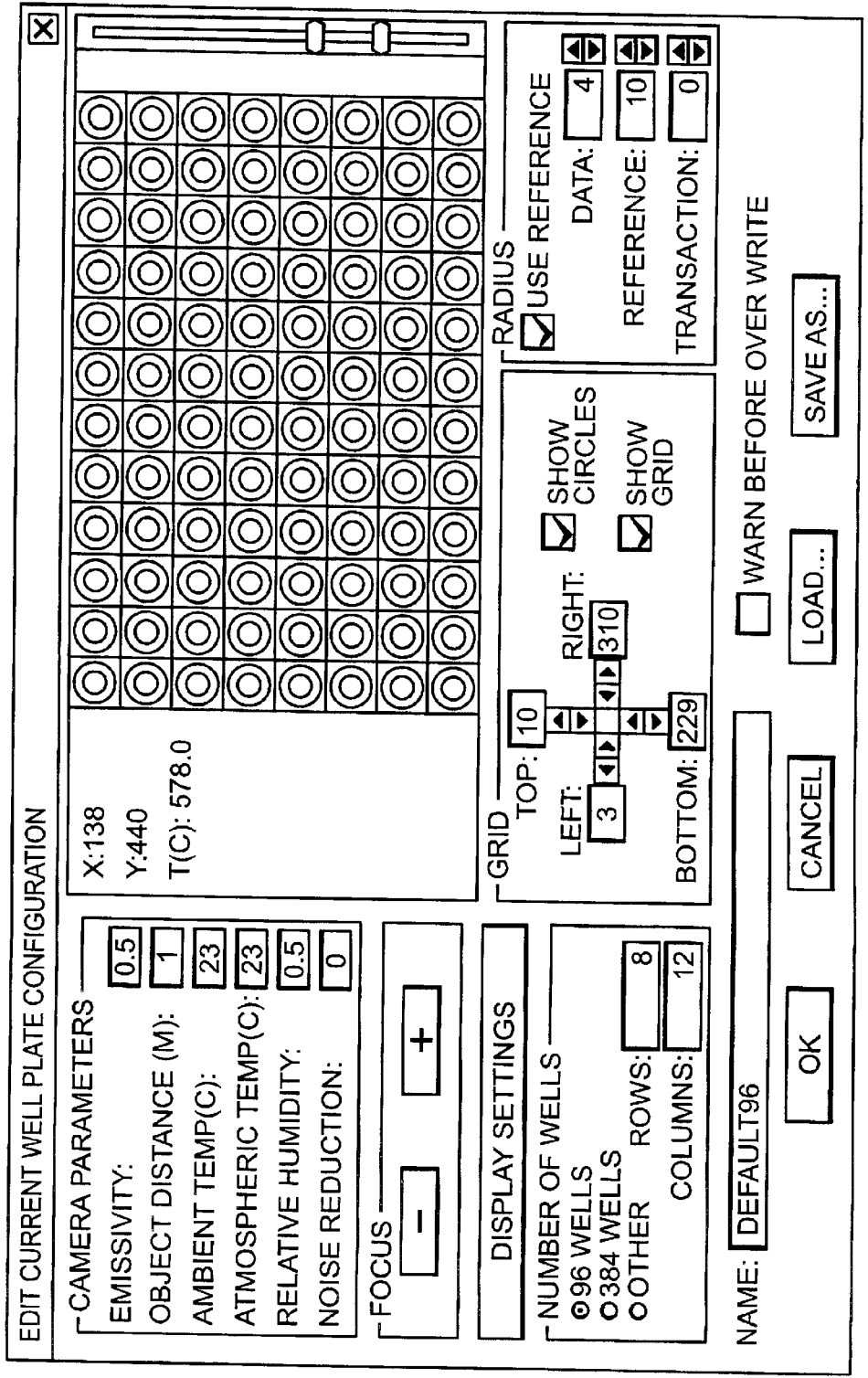
FIG. 13 is a software screen for use in defining selected characteristics of the reference region.

FIGS. 12 and 13 show software screens for collecting, displaying, and/or calibrating data relating to the measurement and reference regions. The top screen shows the application screen for collecting data using the circular reference around the perimeter of the measurement region. The bottom screen shot shows the setup window for defining the characteristics of the reference. These screens again may include one or more data presentation fields and one or more software switches, among others. Moreover, these screens may permit recording and/or reporting of system parameters, such as emissivity, object distance, ambient temperature, relative humidity, noise reduction methods, and/or sample holder format, among others.

Example 10

This example describes noise-reduction methods provided by aspects of the invention, particularly noise-reduction methods relating to temporal and spatial noise.

The noise-reduction methods may include (1) converting detected thermal infrared radiation to a signal, and (2) processing the signal to reduce the proportion of the signal that is attributable to noise. The step of processing the signal may include a step of (1) temporally averaging the signal comprising computing a quantity based on distinguishable components of the signal representing thermal infrared radiation detected from the same sample at different times, and/or (2) replacing at least a portion of the signal with a revised portion formed from distinguishable components of the signal representing thermal infrared radiation detected from the same position or positions in the sample at different times. Alternatively, or in addition, the step of processing the signal may include a step of (1) spatially averaging the signal comprising computing a quantity based on distinguishable components of the signal representing thermal infrared radiation detected from different portions of the same sample, and/or (2) replacing at least a portion of the signal with a revised portion formed from distinguishable components of the signal representing thermal infrared radiation detected from the different positions in the sample at the same time.

The time-based methods may be used to reduce temporal noise, among others, as described above in Section B. These methods may involve replacing a portion of the signal with a revised portion formed for one or more positions in one or more samples from distinguishable components of the signal representing thermal infrared radiation detected from at least two, four, eight, or sixteen different times, among others. These methods also may involve forming a weighted average of distinguishable components of the signal representing thermal infrared radiation detected from the same position in the sample at different times, for example, by application of frame-averaging. In some embodiments, these methods may be adapted preferentially to reduce high-frequency temporal noise in the signal, for example, by application of a low-pass temporal filter and/or by replacing a relatively higher number of time data points with a relatively smaller number of time data points.

The space-based methods may be used analogously to reduce spatial noise, among others, as described above in Section B. These methods may involve replacing a portion of the signal with a revised portion formed at one or more different times from distinguishable components of the signal representing thermal infrared radiation detected from at least two, four, five, nine, or sixteen different positions in the sample, among others, and/or from different samples. These methods also may involve forming a weighted average of distinguishable components of the signal representing thermal infrared radiation detected from different positions in the sample at the same time. In some embodiments, these methods may be adapted preferentially to reduce high-frequency spatial noise in the signal, for example, by application of a low-pass spatial filter and/or by replacing a relatively higher number of spatial data points with a relatively smaller number of spatial data points.

The time-based and space-based methods may be used alone and/or together. Moreover, in many applications, both types of methods may be applied more than once to a particular signal. For example, a signal may be processed by replacing a portion of the signal with a revised portion formed from distinguishable components of the signal representing thermal infrared radiation detected from the same sample at different times, and then re-processed by replacing at least a portion of the revised portion of the signal with a re-revised portion formed from distinguishable components of the revised portion representing thermal infrared radiation detected from the same sample at different times. Here, the times used to process the signal and the times used to re-process the signal may be the same or different.

The noise-reduction methods also may include (1) detecting thermal infrared radiation transmitted from a reference region adjacent a sample, and (2) constructing a sample signal characteristic of the thermal infrared radiation detected from the sample based on the thermal infrared radiation detected from the sample (e.g., as embodied in the processed signal) and the adjacent reference region. The reference region may comprise an annular portion of the sample plate distributed adjacent a perimeter and/or about a central or optical axis of the sample well.

The noise-reduction methods also may include repeating the steps of detecting, converting, and/or processing for a plurality of samples and/or reference regions. Thus, the methods may include (1) detecting thermal infrared radiation transmitted from a plurality of samples positioned at a corresponding plurality of sample sites associated with the sample holder, (2) converting the thermal infrared radiation detected from each sample to a corresponding signal, and (3) processing each signal to reduce noise, as described above. The thermal infrared radiation from each sample may be detected and/or processed simultaneously and/or sequentially. The signals may be adjusted before and/or after processing so that each has the same preselected value at the same preselected time. The preselected value may be zero, among others, and/or the preselected time may be zero, among others.

The disclosure set forth above encompasses multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious and directed to one of the inventions. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed through amendment of the present claims or through presentation of new claims in this or a related application. Such claims, whether directed to a different invention or to the same invention, and whether broader, narrower, equal, or different in scope to the original claims, also are regarded as included within the subject matter of the inventions of the present disclosure.

We claim:

1. A method of detecting thermal infrared radiation, comprising:

providing a sample substrate having a plurality of discrete sample sites configured to support a corresponding plurality of samples;

providing an optical device configured preferentially to detect thermal infrared radiation;

detecting thermal infrared radiation transmitted from a sample positioned at a corresponding sample site using the optical device;

converting the detected thermal infrared radiation to a signal; and processing the signal to reduce noise by replacing at least a portion of the signal with a revised portion formed from distinguishable components of the signal representing thermal infrared radiation detected from the same position in the sample at different times or from different positions in the sample at the same time.

2. The method of claim 1, further comprising correlating the processed signal with the progress of a chemical or physiological reaction occurring in the sample.

3. The method of claim 1, where the sample sites keep at least a portion of each sample from mixing with at least a portion of each other sample.

4. The method of claim 1, where the sample substrate is a microarray.

5. The method of claim 1, where the sample sites keep each portion of each sample from mixing with each portion of each other sample.

6. The method of claim 1, where the sample substrate is a microplate, and where the sample sites are microplate wells.

7. The method of claim 1, where the number of sample sites is selected from the group consisting of 96, 384, 768, 1536, 3456, and 9600.

8. The method of claim 1, where the density of sample sites is at least about 1 well per 81 $mm^2$.

9. The method of claim 1, where the optical device comprises:

an examination site; and a detector configured to receive and preferentially to detect thermal infrared radiation transmitted from a sample positioned at a sample site at the examination site.

10. The method of claim 1, further comprising shielding the sample from incident radiation to reduce the proportion of the signal arising from transmission, reflection, and/or photoluminescence from the sample.

11. The method of claim 1, further comprising filtering the radiation transmitted from the sample to extract thermal infrared radiation prior to the step of detecting thermal infrared radiation.

12. The method of claim 1, where at least about half of the thermal infrared radiation detected by the optical device has a wavelength between about 3 micrometers and about 5 micrometers.

13. The method of claim 1, where at least about half of the thermal infrared radiation detected by the optical device has a wavelength between about 7 micrometers and about 14 micrometers.

14. The method of claim 1, where the processed signal is representative of the temperature of the sample.

15. The method of claim 1, where the revised portion is formed from distinguishable components of the signal representing thermal infrared radiation detected from the same position in the sample at different times and from different positions in the sample at the same time.

16. The method of claim 1, where the revised portion is formed from distinguishable components of the signal representing thermal infrared radiation detected from the same position in the sample at different times and not from different positions in the sample at the same time.

17. The method of claim 1, where the revised portion is formed from distinguishable components of the signal representing thermal infrared radiation detected from different positions in the sample at the same time and not from the same position in the sample at different times.

18. The method of claim 1, where the revised portion is formed for at least one position in the sample from distinguishable components of the signal from at least four different times.

19. The method of claim 18, where the revised portion is formed for at least one position in the sample from distinguishable components of the signal from at least sixteen different times.

20. The method of claim 1, where the revised portion is formed for at least one time from distinguishable components of the signal from at least four different positions in the sample.

21. The method of claim 18, where the revised portion is formed for at least one time from distinguishable components of the signal from at least nine different positions in the sample.

22. The method of claim 1, where the step of processing is adapted preferentially to reduce high-frequency temporal noise in the signal.

23. The method of claim 1, where the step of processing is adapted preferentially to reduce high-frequency spatial noise in the signal.

24. The method of claim 1, where the step of processing the signal includes the step of forming a weighted average of distinguishable components of the signal representing thermal infrared radiation detected from the same position in the sample at different times.

25. The method of claim 1, where the step of processing the signal includes the step of forming a weighted average of distinguishable components of the signal representing thermal infrared radiation detected from different positions in the sample at the same time.

26. The method of claim 1, the revised portion being formed from distinguishable components of the signal representing thermal infrared radiation detected from the same sample at different times, further comprising re-processing the signal by replacing at least a portion of the revised portion of the signal with a re-revised portion formed from distinguishable components of the revised portion representing thermal infrared radiation detected from the same sample at different times, where the times used to process the signal and the times used to re-process the signal may be the same or different.

27. The method of claim 1, where the signal is an image, and where the step of processing the signal includes forming a frame-average of a plurality of images.

28. The method of claim 1, where the signal comprises a set of discrete data points, and where the step of processing the signal reduces the number of data points.

29. The method of claim 1, further comprising:

detecting thermal infrared radiation transmitted from a reference region adjacent the sample site; and constructing a sample signal characteristic of the thermal infrared radiation detected from the sample based on the processed signal and the thermal infrared radiation detected from the reference region.

30. The method of claim 29, the sample sites having a central axis, where the thermal reference region includes an annular emissive reference surface positioned about the central axis of each sample site.

31. The method of claim 29, where the thermal reference region has an emissivity of at least about 0.5.

32. The method of claim 29, further comprising repeating the steps of detecting thermal infrared radiation transmitted from a sample and detecting thermal infrared radiation transmitted from an adjacent reference region for a plurality of samples positioned at a corresponding plurality of the sample sites associated with the sample plate.

33. The method of claim 1, further comprising covering the sample wells to reduce evaporative heat loss from the samples.

34. The method of claim 1, further comprising repeating the steps of detecting, converting, and processing for a plurality of samples positioned at a corresponding plurality of the sample sites associated with the sample substrate.

35. The method of claim 34, where the thermal infrared radiation is detected simultaneously from the plurality of samples.

36. The method of claim 34, where the thermal infrared radiation is detected sequentially from the plurality of samples.

37. The method of claim 34, further comprising adjusting the processed signal corresponding to each sample so that each processed signal has the same preselected value at the same preselected time.

38. The method of claim 37, where the preselected value is zero.

39. The method of claim 37, where the preselected time is zero.

40. The method of claim 34, further comprising displaying the processed signals graphically in a manner representative of the arrangement of the corresponding sample sites on the substrate.

41. The method of claim 34, where the processed signal comprises a single value for each sample at each time.

42. A system for detecting thermal infrared radiation, comprising:
   a sample substrate having a plurality of discrete sample sites configured to support a corresponding plurality of samples;
   an optical device having an examination site and a detector, where the optical device is configured preferentially to detect thermal infrared radiation transmitted from a sample positioned at a corresponding sample site at the examination site; and
   a processor incorporating instructions for and capable of carrying out the function of reducing noise by replacing at least a portion of the signal with a revised portion formed from distinguishable components of the signal representing thermal infrared radiation detected from the same position in the sample at different times or from different positions in the sample at the same time.

43. A system for detecting thermal infrared radiation, comprising:
   means for supporting a plurality of samples at a corresponding plurality of discrete sample sites;
   means for preferentially detecting thermal infrared radiation transmitted from a sample positioned at a corresponding sample site; and
   means for reducing noise by replacing at least a portion of the signal with a revised portion formed from distinguishable components of the signal representing thermal infrared radiation detected from the same position in the sample at different times or from different positions in the sample at the same time.

* * * * *